US010712347B2

(12) United States Patent
Strano et al.

(10) Patent No.: US 10,712,347 B2
(45) Date of Patent: Jul. 14, 2020

(54) SENSORS EMPLOYING SINGLE-WALLED CARBON NANOTUBES

(71) Applicant: THE BOARD OF TRUSTEES OF THE UNIVERSITY OF ILLINOIS, Urbana, IL (US)

(72) Inventors: Michael S. Strano, Lexington, MA (US); Seunghyun Baik, Champaign, IL (US); Paul Barone, Jamaica Plain, MA (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 14/320,480

(22) Filed: Jun. 30, 2014

(65) Prior Publication Data
US 2014/0308681 A1    Oct. 16, 2014

Related U.S. Application Data

(63) Continuation of application No. 11/187,706, filed on Jul. 22, 2005, now Pat. No. 8,765,488.
(Continued)

(51) Int. Cl.
*G01N 33/66* (2006.01)
*B82Y 30/00* (2011.01)
(Continued)

(52) U.S. Cl.
CPC .............. *G01N 33/66* (2013.01); *B82Y 15/00* (2013.01); *B82Y 30/00* (2013.01); *G01N 33/551* (2013.01)

(58) Field of Classification Search
CPC ...... G01N 33/66; G01N 33/551; B82Y 30/00; B82Y 15/00
See application file for complete search history.

(56) References Cited

U.S. PATENT DOCUMENTS 4,238,195 A    12/1980  Boguslaski et al.
4,344,438 A    8/1982   Schultz
(Continued)

FOREIGN PATENT DOCUMENTS

WO    WO 00/017102    3/2000
WO    WO 00/026138    5/2000
(Continued)

OTHER PUBLICATIONS

O'Connell et al., "Band Gap Fluorescence from Individual Single-Walled Carbon Nanotubes", Science (Jul. 26, 2002) 297:593-596.*
(Continued)

*Primary Examiner* — Melanie Brown
(74) *Attorney, Agent, or Firm* — Steptoe & Johnson LLP

(57) ABSTRACT

Sensing compositions, sensing element, sensing systems and sensing devices for the detection and/or quantitation of one or more analytes. Compositions comprising carbon nanotubes in which the carbon nanotubes retain their ability to luminesce and in which that luminescence is rendered selectively sensitive to the presence of an analyte. Compositions comprising individually dispersed carbon nanotubes, which are electronically isolated from other carbon nanotubes, yet which are associated with chemical selective species, such as polymers, particularly biological polymers, for example proteins, which can interact selectively with, or more specifically selectivity bind to, an analyte of interest. Chemically selective species bind, preferably non-covalently, to the carbon nanotube and function to provide for analyte selectivity. Chemically selective species include polymers to which one or more chemically selective groups are covalently attached. Chemically selective polymers include, for example, proteins and polysaccharides.

22 Claims, 16 Drawing Sheets

Related U.S. Application Data

(60) Provisional application No. 60/590,865, filed on Jul. 22, 2004.

(51) Int. Cl.
*G01N 33/551* (2006.01)
*B82Y 15/00* (2011.01)

(56) References Cited

U.S. PATENT DOCUMENTS

| | | | |
|---|---|---|---|
| 4,588,681 A | 5/1986 | Sawada et al. | |
| 4,830,959 A | 5/1989 | McNeil et al. | |
| 4,837,478 A | 6/1989 | Anzai et al. | |
| 5,413,690 A | 5/1995 | Kost et al. | |
| 5,645,709 A | 7/1997 | Birch et al. | |
| 5,648,237 A | 7/1997 | Carter | |
| 5,824,470 A | 10/1998 | Baldeschwieler | |
| 5,846,727 A | 12/1998 | Soper et al. | |
| 5,866,434 A | 2/1999 | Massey et al. | |
| 5,877,202 A | 3/1999 | Bitonti et al. | |
| 6,066,448 A | 5/2000 | Wohlstadter et al. | |
| 6,123,819 A | 9/2000 | Peeters | |
| 6,160,030 A | 12/2000 | Chaouk et al. | |
| 6,183,714 B1 | 2/2001 | Smalley et al. | |
| 6,312,896 B1 | 11/2001 | Heroux et al. | |
| 6,362,011 B1 | 3/2002 | Massey et al. | |
| 6,437,329 B1* | 8/2002 | Yedur | B82Y 15/00 250/234 |
| 6,528,020 B1 | 3/2003 | Dai et al. | |
| 6,656,712 B1 | 12/2003 | Balavoine et al. | |
| 6,692,717 B1 | 2/2004 | Smalley et al. | |
| 6,719,147 B2 | 4/2004 | Strano et al. | |
| 6,761,870 B1 | 7/2004 | Smalley et al. | |
| 6,821,730 B2 | 11/2004 | Hannah | |
| 6,919,730 B2 | 7/2005 | Cole et al. | |
| 7,290,667 B1* | 11/2007 | Bakajin | B01D 39/06 210/500.22 |
| 8,518,716 B2 | 8/2013 | Hubel et al. | |
| 8,765,488 B2* | 7/2014 | Strano | B82Y 15/00 435/14 |
| 2002/0090330 A1 | 7/2002 | Smalley et al. | |
| 2002/0117659 A1* | 8/2002 | Lieber | B82Y 10/00 257/14 |
| 2002/0155425 A1* | 10/2002 | Han | A61B 5/14532 435/4 |
| 2002/0179434 A1 | 12/2002 | Dai et al. | |
| 2003/0012723 A1 | 1/2003 | Clarke | |
| 2003/0089899 A1 | 5/2003 | Lieber et al. | |
| 2003/0113714 A1 | 6/2003 | Belcher et al. | |
| 2003/0134267 A1 | 7/2003 | Kang et al. | |
| 2003/0134433 A1 | 7/2003 | Gabriel et al. | |
| 2003/0138973 A1* | 7/2003 | Wagner | B82Y 15/00 436/518 |
| 2003/0218224 A1 | 11/2003 | Schlaf et al. | |
| 2004/0005723 A1 | 1/2004 | Empedocles et al. | |
| 2004/0022677 A1 | 2/2004 | Wohlstadter et al. | |
| 2004/0038251 A1* | 2/2004 | Smalley | B82Y 15/00 435/6.11 |
| 2004/0124020 A1* | 7/2004 | Leifert | B60L 7/22 180/65.1 |
| 2004/0198705 A1* | 10/2004 | Willnow | G01N 33/743 514/169 |
| 2004/0235016 A1* | 11/2004 | Hamers | B82Y 5/00 435/6.19 |
| 2005/0100960 A1* | 5/2005 | Dai | B82Y 10/00 435/7.1 |
| 2005/0124020 A1* | 6/2005 | Lee | B82Y 30/00 435/14 |
| 2005/0265914 A1* | 12/2005 | Gu | B82Y 15/00 423/445 B |
| 2005/0277160 A1 | 12/2005 | Shiba et al. | |
| 2006/0199770 A1* | 9/2006 | Bianco | A61K 47/48238 424/486 |

FOREIGN PATENT DOCUMENTS

| | | |
|---|---|---|
| WO | WO 01/44796 | 6/2001 |
| WO | WO 02/016257 | 2/2002 |
| WO | WO 02/095099 | 11/2002 |
| WO | WO 03/050332 | 6/2003 |
| WO | WO 03/084869 | 10/2003 |
| WO | WO 03/102020 | 12/2003 |

OTHER PUBLICATIONS

J. Kong et al., "Nanotube Molecular Wires as Chemical Sensors", Science, vol. 287, Jan. 28, 2000, pp. 622-625.

E. Csöregi et al., "Design, Characterization, and One-Point in Vivo Calibration of a Subcutaneously Implanted Glucose Electrode", Analytical Chemistry, vol. 66, No. 19, Oct. 1, 1994, pp. 3131-3138.

Strano, "Probing chiral selective reactions using a revised kataura plot for the interpretation of single-walled carbon nanotube spectroscopy," J. Am. Chem. Soc., Nov. 22, 2003, vol. 125, pp. 16148-16153.

Webster's New Collegiate Dictionary, G & C Merriam Co., Springfield, MA, 1974, p. 306.

Frehill et al., "Interconnecting Carbon Nanotubes With an Inorganic Metal Complex", J. Am. Chem. Soc., 2002, vol. 124, pp. 13694-13695.

Zhu et al., "Fluorescent Chromophore Functionalized Single-Wall Carbon Nanotubes With Minimal Alteration to Their Characteristic One-Dimensional Electronic States", J. Mater. Chern., 2003, vol. 13, pp. 2196-2201

Ando (1997), "Excitons in Carbon Nanotubes" J. Phys. Soc. Jap. 66:1066-1073.

Bachilo et al., (2003), "Narrow (n,m)-Distribution of Single-Walled Carbon Nanotubes Grown Using a Solid Supported Catalyst", J. Am. Chern. Soc. 125:11186-11187.

Bachilo et al., (2002), "Structure-Assigned Optical Spectra of Single-Walled Carbon Nanotubes", Science 298:2361-2366.

Bahr et al., (2002), "Covalent Chemistry of Single-Walled Carbon Nanotubes", J. Mat. Chem. 12:1952-1958.

Bahr et al., (2001), "Functionalization of Carbon Nanotubes by Electrochemical Reduction of Aryl Diazonium Salts: Bucky Paper Electrode", J. Am. Chem. Soc.123:6536-6542.

Baker et al., (2002), "Covalently Bonded Adducts of Deoxyribonucleic Acid (DNA) Oligonucleotides with Single-Wall Carbon Nanotubes: Synthesis and Hybridization", Nano Lett. 2(12):1413-1417.

Baker et al., (2003), "Covalently-Linked Adducts of Single-Walled Nanotubes with Biomolecules: Synthesis, Hybridization, and Biologically-Directed Surface Assembly", Mat. Res. Symp. Proc. 737:F4.6.1-F4.6.7.

Balavoine et al., (1999), "Helical Crystallization of Proteins on Carbon Nanotubes: A First Step Towards the Development of New Biosensors", Angew. Chem. Int. Ed. 38:1912-1915.

Ballerstadt and Schultz (2000) "A Fluorescence Affinity Hollow Fiber Sensor for Continuous Transdermal Glucose Monitoring", Anal. Chem. 72:4185-4192.

Barone et al., (2005), "Near-infrared Optical Sensors Based on Single-Walled Carbon Nanotubes", Nature Mater. 4, 86-92.

Beyer et al., (2001) "Recording of Subcutaneous Glucose Dynamics by a Viscometric Affinity Sensor", Diabetologia 44: 416-423.

Bronikowski et al., (2001), "Gas-Phase Production of Carbon Single-Walled Nanotubes from Carbon Monoxide via the HiPco Process: A Parametric Study", J. Vac. Sci. Tech. A. 19(4): 1800-1805.

Cassell et al., (1999), "Directed Growth of Free-Standing Single-Walled Carbon Nanotubes", J. Am. Chem. Soc. 121:7975-7976.

Cassell et al., (1999), "Large Scale CVD Synthesis of Single Walled Carbon Nanotubes", J. Phys. Chem. B 103:6484-6492.

Chen et al., (2001), "Dissolution of Full-Length Single-Walled Carbon Nanotubes", J. Phys. Chern. B 105(13):2525-2528.

Chen et al., (2003), "Noncovalent Functionalization of Carbon Nanotubes for Highly Specific Electronic Biosensors", Proc. Natl. Acad. Sci. USA 100:4984-4989.

(56) References Cited

OTHER PUBLICATIONS

Chen et al., (1998), "Solution Properties of Single-Walled Carbon Nanotubes", Science 282:95-98.
Chen et al., (2001), "Noncovalent Sidewall Functionalization of Single-Walled Carbon Nanotubes for Protein Immobilization", J. Am. Chem. Soc. 123:3838-3839.
Cherukuri et al., (2004), "Near-Infrared Fluorescence Microscopy of Single-Walled Carbon Nanotubes in Phagocytic Cells", J. Am. Chem. Soc. 126:15638-15639.
Dai et al., (1999), "Controlled Chemical Routes to Nanotube Architectures, Physics, and Devices", J. Phys. Chem. B 103:11246-11255.
D'Auria et al., (1999), "The Fluorescence Emission of the Apo-Glucose Oxidase from Aspergillus niger as a Probe to Estimate Glucose Concentrations", Biochem. Biophys. Res. Commun. 263:550-553.
Dou et al., (1998), "Raman Study of Enzyme Reactions Using Potassium Ferricyanide as a Reaction Mediator: Quantitative Analysis of Substrates and Measurement of Enzyme Activity for Glucose Oxidase and Lactate Oxidase", Appl. Spectroscopy 52:815-819.
Durkop et al., (Jan. 2004), "Extraordinary Mobility in Semiconducting Carbon Nanotubes", Nano Lett. 4:35-39.
Gudiksen et al., (2002), "Growth of Nanowire Supenattice Structures for Nanoscale Photonics and Electronics", Nature 415:617-620.
Hartschuh et al., (2003), "Simultaneous Fluorescence and Raman Scattering from Single Carbon Nanotubes", Science 301:1354-1356.
Heller et al., (1999), "Implanted Electrochemical Glucose Sensors for the Management of Diabetes", Ann. Rev. Biomed. Eng. 1: 153-175.
Huang et al., (2002), "Sonication-Assisted Functionalization and Solubilization of Carbon Nanotubes", Nano Lett. 2(3):231-234.
Journet, et al., (1997), "Large-Scale Production of Single-Walled Carbon Nanotubes by the Electric-Arc Technique", Nature 388:756-758.
Kane and Mele (May 2003), "Ratio Problem in Single Carbon Nanotube Fluorescence Spectroscopy", Phys. Review Letts. 90:207401.
Kim et al., (Jan. 2004), "Near-infrared fluorescent type II quantum dots for sentinel lymph node mapping", Nature Biotech. 22:93-97.
Kong et al., (1998), "Synthesis of Individual Single-Walled Carbon Nanotubes on Patterned Silicon Wafers", Nature 395:878-881.
Kong et al., (1998), "Chemical Vapor Deposition of Methane for Single-Walled Carbon Nanotubes", Chem. Phys. Lett. 292:567-574.
Krupke et al., (Jun. 2003), "Separation of Metallic from Semiconducting Single-Walled Carbon Nanotubes", Science Express.
Li et al., (2001), "Preparation of Monodispersed Fe-Mo Nanoparticles as the Catalyst for CVD Synthesis of Carbon Nanotubes", Chem. Mater. 13: 1008-1014.
Li et al., (Jul. 2003), "Carbon Nanotubes Sensors for Gas and Organic Vapor Detection", Nano. Lett. 3:929-933.
Lin et al. (Feb. 2004), "Glucose Biosensors Based on Carbon Nanotube Nanoelectrode Ensembles", Nano. Lett. 4(2):191-195.
McCartney et al., (2001) "Near-Infrared Fluorescence Lifetime Assay for Serum Glucose Based on Allophycocyanin-Labled Concanavalin A", Anal. Biochem. 292:216-221.
Moore et al., (Oct. 2003), "Individually Suspended Single-Walled Carbon Nanotubes in Various Surfactants", Nano Lett. 3:1379-1382.
Nakashima et al., (2002), "Water-Soluble Single-Walled Carbon Nanotubes via Noncovalent Sidewall-Functionalization with a Pyrene-Carrying Ammonium Ion", Chem. Lett. 6:638-639.

Nikolaev et al., (1999), "Gas-Phase Catalytic Growth of Single-Walled Carbon Nanotubes from Carbon Monoxide", Chem. Phys. Lett. 313:91-97.
O'Connell et al., (2002), "Band Gap Fluorescence from Individual Single-Walled Carbon Nanotubes", Science 297:593-596.
Prakash et al., (Aug. 2003), "Visualization of Individual Carbon Nanotubes with Fluorescence Microscopy Using Conventional Fluorophores", Appl. Phys. Lett.83(6):1219-1221.
Rebrin et al., (1992), "Subcutaneous Glucose Monitoring by Means of Electrochemical Sensors—Fiction or Reality", J. Biomed. Eng. 14:33-40.
Salins et al., (2001), "A Novel Reagentless Sensing System for Measuring Glucose Based on the Galactose/Glucose-Binding Protein", Anal. Biochem. 294:19-26.
Saxena et al., (Jul. 2003), "Degradation kinetics of indocyanine green in aqueous Solution", J. Pharm. Sci. 92:2090-2097.
Schoonjans et al., (2000), "Fab Chains as an Efficient Heterodimerization Scaffold for the Production of Recombinant Bispecific and Trispecific Antibody Derivatives", J. Immunol. 165(12):7050-7057.
Schultz et al., (1982), "Affinity Sensor: A New Technique for Developing Implantable Sensors for Glucose and Other Metabolites", Diabetes Care 5:245-253 (Abstract Only).
Shim et al., (2002), "Functionalization of Carbon Nanotubes for Biocompatibility and Biomolecular Recognition", Nano Lett. 2(4):285-288.
Strano et al., (Feb. 2003), "The Role of Surfactant Adsorption During Ultrasonication in the Dispersion of Single-Walled Carbon Nanotubes", J. Nanosci. Nanotechnol. .3:81-86.
Strano et al., (Sep. 2003), "Electronic Structure Control of Single-Walled Carbon Nanotube Functionalization", Science 301:1519-1522.
Strano et al., (Jul. 2003), "Reversible, Band-Gap-Selective Protonation of Single-Walled Carbon Nanotubes in Solution", J. Phys. Chem. B 107:6979-6985.
Strano et at., (Aug. 2003) "Assignment of (n, m) Raman and Optical Features of Metallic Single-Walled Carbon Nanotubes", Nano Letters 3:1091-1096.
Thess et al., (1996), "Crystalline Ropes of Metallic Carbon Nanotubes", Science 273:483.-487.
Waynant et al., (1998), "Overview of Non-Invasive Fluid Glucose Measurement Using Optical Techniques to Maintain Glucose Control in Diabetes Mellitus", LEOS Newsletter 12 (2) published by the IEEE Lasers and Electrooptics Society (www.ileos.org).
Weisman (2004), "Simplifying Carbon Nanotube Identification", The Industrial Physicist Feb./Mar.:24-27.
Worn et al., (1998), "An Intrinsically Stable Antibody scFv Fragment can Tolerate the Loss of Both Disulfide Bonds and Fold Correctly", FEBS Lett. 427(3):357-361.
Xia et al., (1999), "Structure and Function of Ferricyanide in the Formation of Chromate Conversion Coatings on Aluminum Aircraft Alloy", J. Electrochem. Soc. 146:3696-3701.
Zheng et al., (Nov. 2003), "Structure-Based Carbon Nanotube Sorting by Sequence-Dependent DNA Assembly", Science 302:1545-1548.
Zheng et al., (May 2003), "DNA-Assisted Dispersion and Separation of Carbon Nanotubes", Nature Mater. 2:338-342.
Zinn et al., (2003), "Flexible Transistors with High Carrier Mabilities Made from Carbon Nanotubes", MRS Bull. November.:789-796.
Rolinski et al., "A time-resollved near-infrared fluorescence assay for glucose opportunities for trans-dermal sensing", 2000, J.Photochem. Photobiol. B: Biol., vol. 54, p. 26-34.
Russell et al., "A fluorescence-based glucose biosensor using Concanavalin A and dextran encapsulated in a poly(ethylene glycol) hydrogel", 1999, Anal. Chem., vol. 71, pp. 3126-3132.

\* cited by examiner

Fig. 2A
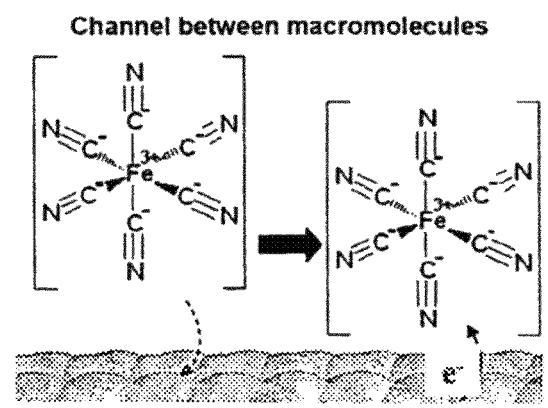
Fig. 2B
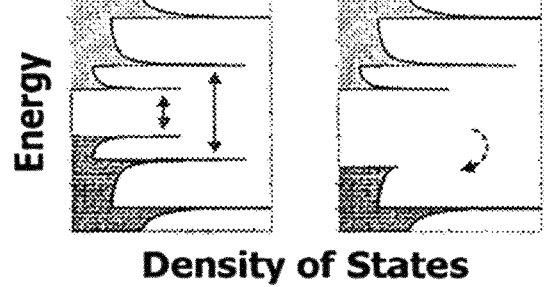
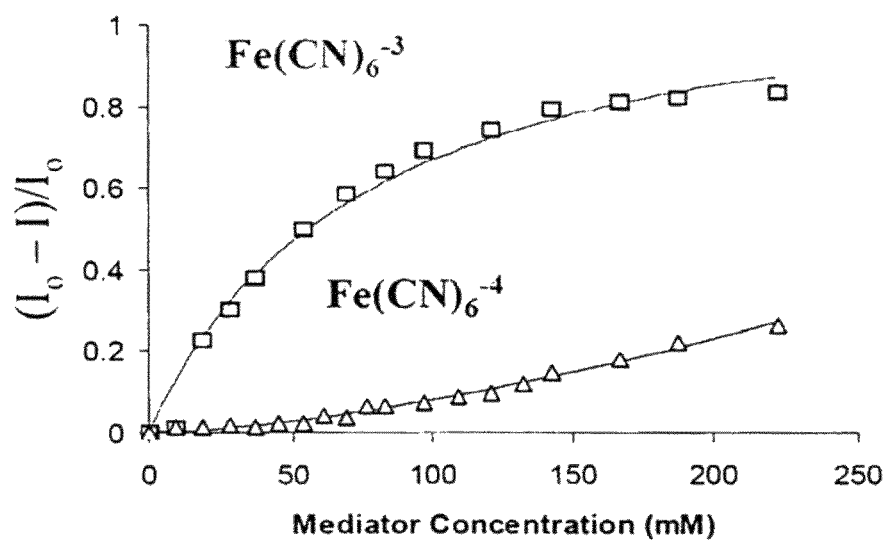
Fig. 2C

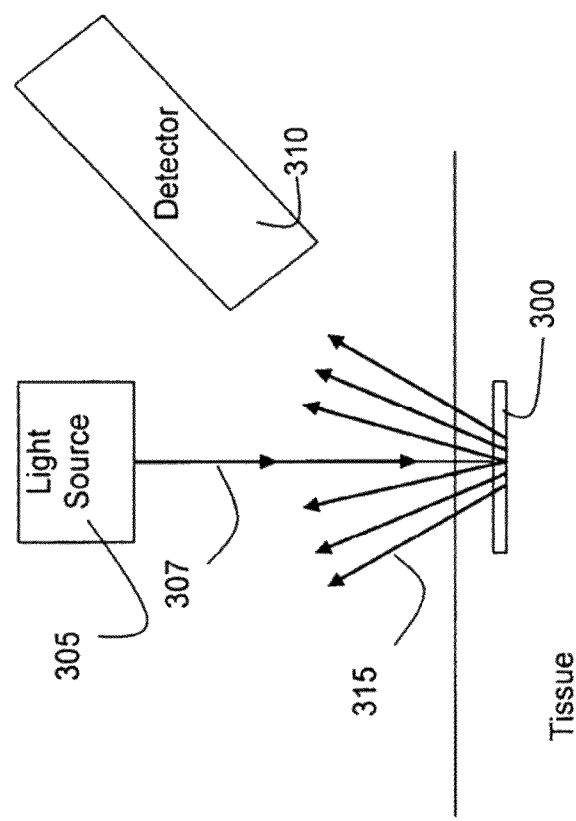

SENSORS EMPLOYING SINGLE-WALLED CARBON NANOTUBES

CROSS-REFERENCE TO RELATED APPLICATIONS

This application is a continuation of claims U.S. application Ser. No. 11/187,706, filed Jul. 22, 2005, which takes priority from U.S. Provisional Application Ser. No. 60/590,865, filed Jul. 22, 2004, each of which is incorporated by reference in its entirety.

STATEMENT REGARDING FEDERALLY SPONSORED RESEARCH

This invention was made through funding from the United States government under National Science Foundation grant number CTS-43330350. The United States government has certain rights in this invention.

BACKGROUND OF THE INVENTION

Carbon nanotubes (1, 2) and semi-conducting nanowires (3) hold particular advantage in sensor applications because their 1-D electronic structure renders electron transport more sensitive to scattering from adsorbates than intrinsic mechanisms (2, 4, 5). Hence, these materials have spawned a host of new conductimetric sensors and array elements (3, 5, 6). Recent advances in the understanding of their optical properties (10, 11, 23) offer the possibility of using such materials as solution phase sensors (7, 8) that respond to analyte adsorption by modulation of optical properties, e.g., modulation of fluorescence emission. Such sensors could be implanted, for example, into human tissue (9) to provide real-time information about biochemical concentrations non-invasively.

Carbon nanotubes fluoresce in the near infrared (10, 11) and certain types (e.g., single walled carbon nanotubes (SWNTs) fluoresce from 900 to 1600 nm) do so in a region where human tissue and fluids, e.g., whole blood, (12) are particularly transparent to emission due to greater penetration and reduced auto-fluorescent background. Furthermore, SWNTs have particular advantage as sensing elements because all atoms of the nanotube are surface atoms making the nanotube especially sensitive to surface adsorption events. However, the ability to design sensors from carbon nanotubes is limited by fundamental limitations in our current ability to simultaneously control the electronic, chemical and colloidal properties of nanoparticle systems. Addition information on the properties of carbon nanotubes is found in the art (52-57.)

For use in selective optical sensor applications for the detection of analytes, carbon nanotubes must retain their ability to luminesce, they must be capable of interacting selectively with the analyte to be detected, and the selective interaction with the analyte must affect carbon nanotube luminescence. Nanotubes in electrical contact with each other do not luminesce because the excited state is depopulated non-irradiatively through inter-tube energy transfer (10). However, van der Waals forces provide large thermodynamic driving forces for aggregation of carbon nanotubes. For nanotubes to luminesce, they must be colloidally stabilized (to minimize or avoid aggregation). Individual fluorescent carbon nanotubes have been suspended after high energy ultrasonication using charged surfactants (10, 11, 13), non-ionic polymers (10, 22), and certain DNA sequences (14, 15). However, these interfaces interfere with the adsorption of charged reagents (17, 15) either via columbic interactions, or steric repulsion.

PCT published application WO03/050332 relates to the preparation of stable carbon nanotube dispersions in liquids. PCT published application WO02/095099 relates to noncovalent sidewall functionalization of carbon nanotubes.

PCT published application WO02/16257 relates to polymer wrapped single wall carbon nanotubes.

PCT published application WO03/102020 reports a method for obtaining peptides which bind to carbon nanotubes and other carbon nanostructures. Libraries containing peptides, typically a random mixture of peptides, are selected for their binding affinity for carbon nanotubes. Details of the method are given. A number of peptides of specific peptide sequence were identified as having binding affinity for carbon nanostructures, including carbon nanotubes. The sequences of a number of such peptides, particularly a set of peptides having 12 amino acids, were provided in the published application.

In addition, dispersed nanotubes exhibit more prominent resonant Raman scatter which is more sensitive to the environment of the nanotube (17), which may be useful in sensing applications.

Functionality must be associated with the carbon nanotube to provide for selective interaction with analytes. The inherent selectivities of biological molecules might, for example, be employed to provide for selective interaction of carbon nanotubes with analytes. However, to remain useful for sensing applications, nanotube functionalization must not disrupt nanotube optical properties (5). While it is possible to chemically attach functional groups to singly dispersed nanotubes (16), covalent functionalization of carbon nanotubes necessarily disrupts the 1-D electronic structure and desired optical properties (5, 16, 23, 24). Functionalization chemistries necessarily result in a rupturing of the conjugated π-cloud along the nanotube, disrupt its optical transitions and destroy fluorescence. Non-covalent modification using electroactive species, although difficult to control (17), provide a means of both preserving the carbon nanotube electronic structure (since no bonds are broken) and creating sites for selective binding.

The current state of carbon nanotube chemistry is therefore paradoxical: one must chemically modify the nanotube to impart desired functionality and selectivity toward analytes, but in doing so the 1-D electronic structure is disrupted destroying the ability to detect analyte interaction. Additionally, an encapsulating phase (e.g., surfactant) must be used to isolate the nanotube for colloidal stability and retention of fluorescence, and yet the stabilized nanotube must be accessible to facilitating molecular recognition.

The present invention provides solutions to the limitations discussed above and provides optical sensors and methods for the selective detection of analytes employing carbon nanotubes, particularly SWNTs.

SUMMARY OF THE INVENTION

This invention provides compositions comprising carbon nanotubes in which the carbon nanotubes retain their ability to luminesce and in which that luminescence is rendered selectively sensitive to the presence of an analyte. More specifically, the invention provides compositions comprising individually dispersed carbon nanotubes, which are electronically isolated from other carbon nanotubes, yet which are associated with chemical selective species, such as polymers, particularly biological polymers, for example proteins, which can interact selectively with, or more specifically selectivity bind to, an analyte. Chemically selective species bind, preferably non-covalently, to the carbon nanotube and function to provide for analyte selectivity. Chemically selective species include polymers to which one or more chemically selective groups are covalently attached.

Chemically selective species also include polymers which are inherently chemically selective in that they selectively bind to or selectively react with an analyte. Analyte is detected and/or the amount present is measured by changes in nanotube luminescence. Chemically selective species useful for analyte detection further include polymers which inherently or via one or more covalently attached chemically selective groups competitively interact with (e.g., bind to or react with) another chemical species (for convenience herein called a sensing partner) with which the analyte interacts. For example, the polymer or the attached chemically selective species can compete with the analyte for binding to a binding partner. In another example, the polymer or the attached chemically selective species can compete with the analyte reaction with the sensing partner (e.g., an enzyme). Analyte is detected and/or the amount present is measured by following changes in nanotube luminescence as analyte competes with the chemically selective species with respect to interaction with the sensing partner.

The invention provides analyte sensing compositions comprising individually dispersed carbon nanotubes complexed with one or more chemically selective species. Chemically selective species, can provide, at least in part, for individual dispersion of the carbon nanotubes. The analyte sensing compositions may further comprise additional polymeric species (including proteins (including polypeptides) polysaccharides or non-biological polymers (such as polymeric non-ionic detergents) which function primarily for facilitating individual dispersion of the carbon nanotubes and are not chemically selective species. For use in competitive assays for detection of analyte, analyte sensing compositions may further comprise one or more sensing partners for the analyte.

The interaction of individually dispersed carbon nanotubes with the chemically selective species functions to couple the chemically selective species directly, or indirectly via one or more redox mediators, to the electronic band structure of the nanotube. This coupling allows a specific interaction of the chemically selective species with the analyte to modulate the optical properties of the nanotube. More specifically, individually dispersed semiconducting single walled carbon nanotubes exhibit band gap fluorescence which is photo-induced by irradiation with electromagnetic radiation of appropriate wavelength. A specific interaction of the chemically selective species with the analyte can, for example, modulates nanotube band gap fluorescence affecting fluorescence intensity, e.g., through charge transfer, or shifting the emission wavelength(s), which can be mediated through induced dipole or bathochromic interactions. Interaction of the analyte with the chemically selective species may for example, increase fluorescence intensity, or decrease fluorescence intensity or the interaction may shift one or more wavelengths of fluorescence.

In analyte sensing compositions of this invention, the optical properties of carbon nanotubes are responsive to specific and/or selective interactions, such as binding events (including binding and disruption of binding) or reactions, of the chemically selective species with an analyte. In specific embodiments, the chemically selective species of this invention are biological molecules, particularly proteins, and more specifically proteins that selectively bind to an analyte (e.g., antibodies or antibody fragments) and even more specifically enzymes (e.g., glucose oxidase) which bind to and catalyze a reaction of the analyte. In other specific embodiments, the biological molecule may also be polysaccharides (e.g., a dextran, composed of glucose units) which competitively binds to a binding partner of a saccharide analyte (e.g., glucose). In other specific embodiments, the chemically selective species are polymers, which are not necessarily themselves biological molecules, but which are functionalized to contain chemically selective groups or moieties which are biological molecules (e.g. biotin, ligands for biological receptors, enzyme substrates, etc.).

In specific embodiments, the carbon nanotubes exhibit band gap fluorescence, particularly near-IR fluorescence. In specific embodiments, the carbon nanotubes are single-walled, semiconducting carbon nanotubes. In specific embodiments, the chemically selective species is non-covalently complexed with the carbon nanotube. In specific embodiments, the chemically selective species are enzymes which oxidize the analyte and in which this selective reaction is coupled to the electronic band structure of the carbon nanotube via one or more redox mediators. In specific embodiments for the detection of glucose, the chemically selective species is glucose oxidase and the redox mediator is an electroactive species such as ferricyanide. In other specific embodiments for detection of glucose, the chemically selective species is a dextran (or other polysaccharide that exhibits binding to glucose binding partners) and the sensing partner is a protein that binds to glucose (and dextran) such as concanavalin A (Con A) or apo-glucose oxidase (an inactive form of glucose oxidase which retains binding affinity for glucose).

In a specific embodiment, the invention provides an analyte sensing composition which comprises a semiconducting single-walled carbon nanotube (SWNT) complexed with one or more proteins or one or more polysaccharides (such as a dextran) and dispersed in a liquid or solid phase wherein the SWNT/protein complex or the SWNT/polysaccharide complex exhibits a luminescence response, (e.g., band gap fluorescence, particularly near-IR fluorescence) on excitation with electromagnetic radiation of appropriate wavelength; and wherein at least one of the proteins or one of the polysaccharides complexed with the semiconducting SWNT, which is designated the sensing protein or sensing polysaccharide, respectively, is selected such that the analyte selectively binds to or selectively reacts with the sensing protein or sensing polysaccharide. The selective interaction of the analyte and the sensing protein or sensing polysaccharide directly or indirectly modulates the optical properties of the SWNT/protein or polysaccharide complex, for example, the luminescence response of the SWNT/protein or polysaccharide complex. In specific embodiments, the analyte sensing composition comprises a semiconducting SWNT which is complexed to one or more polymers wherein at least one of the polymers is a chemically selective species.

In specific embodiments, sensing compositions of this invention consist essentially of a semiconducting single-walled carbon nanotube (SWNT) complexed with one or more proteins, one or more polysaccharides or one or more non-biological polymers which is functionalized with one or more chemically selective groups (e.g., biological groups or moieties) wherein the SWNT/polymer complex exhibits band gap fluorescence and wherein at least one of the polymers complexed with the semiconducting is a sensing polymer which selectively binds to or selectively reacts with the analyte and wherein the selective interaction of the analyte and the sensing polymer directly or indirectly modulates the band gap fluorescence response of the SWNT/polymer complex. In specific embodiments, the polymer is one or more proteins or a mixture of one or more proteins with one or more polysaccharide and or one or more non-biological polymers and one or more of the proteins is a sensing protein.

The sensing protein can, in specific embodiments, be an enzyme with which the analyte selectively reacts. In specific embodiments, the enzyme catalyzes an oxidation or a reduction of the analyte. In a specific embodiment, the enzyme generates hydrogen peroxide on reaction with the analyte. In more specific embodiments, the enzyme is an oxidase and the analyte is a substrate for the oxidase. In other specific embodiments, the enzyme (where the analyte is a substrate of the listed enzyme) is selected from the group consisting of a glucose oxidase, a glucose dehydrogenase, a galactose oxidase, a glutamate oxidase, an L-amino acid oxidase, a D-amino acid oxidase, a cholesterol oxidase, a cholesterol esterase, a choline oxidase, a lipoxigenase, a lipoprotein lipase, a glycerol kinase, a glycerol-3-phosphate oxidase, a lactate oxidase, a lactate dehydrogenase, a pyruvate oxidase, an alcohol oxidase, a bilirubin oxidase, a sarcosine oxidase, a uricase (also called a urate oxidase), and an xanthine oxidase. Embodiments in which the sensing protein is an enzyme can be used in various enzyme assays for detection, quantitation or both of analyte, for example, in competitive inhibition assays.

Further the analyte sensing compositions of this invention can be employed to detect analytes that are inhibitors of enzyme activity. In this case, the sensing protein is an enzyme the activity of which is inhibited by the analyte. Analyte sensing compositions for the detection and/or quantitation of an enzyme inhibitor would also comprise an enzyme substrate, present in an amount sufficient to not be limiting to the enzyme reaction. The analyte sensing compositions of this invention can thus be employed to screen for the presence of enzyme inhibitors.

In specific embodiments, the sensing composition also contains a redox mediator in addition to the sensing protein which may be reversibly or irreversible complexed with the semiconducting SWNT. The mediator functions to alter surface charge of the carbon nanotube to modulate the luminescence response of the semiconducting SWNT/protein complex. Most generally, the redox mediator is an electroactive species. In specific embodiments, the redox mediator is an electron acceptor. In specific embodiments, the mediator is a transition metal complex ion. In specific embodiments, the mediator is an electroactive species that is reduced or oxidized by reaction with a product of the reaction of the analyte with a sensing protein. In specific embodiments the mediator is an oxidized species that is reduced by reaction with hydrogen peroxide generated on reaction of the analyte with a sensing protein enzyme. In a more specific embodiment, the mediator is ferricyanate ion or ferrocyanate ion.

In specific embodiments, the analyte is a natural substrate of the enzyme employed as the sensing protein. In specific embodiments, the analyte is not the natural substrate of the enzyme, which can include chemical derivatives of the natural substrate for the enzyme. In specific embodiments, the enzyme is obtained from commercial sources, is isolated from natural sources, or is prepared by recombinant methods. In specific embodiments, the enzyme is a variant, derivative, or semi-synthetic analog of a naturally-occurring enzyme which, for example, has been modified by modification of one or more amino acids to exhibit altered activity, e.g., enhanced activity, compared to the naturally-occurring enzyme, is a deglycosylated form of a naturally-occurring enzyme or a variant or derivative thereof, is formed by reconstitution of an apo-enzyme with its required co-factor (e.g., FAD), is formed by reconstitution of an apo-enzyme with a derivatized co-factor. Enzyme variants, derivatives or semi-synthetic analogs of naturally-occurring enzymes may exhibit altered substrate specificity and/or altered enzyme kinetics compared to naturally-occurring forms of the enzyme.

In other specific embodiments, the sensing protein is a receptor or other binding partner to which the analyte selectively binds. In these cases, the analyte may itself be a ligand or binding partner which selectively binds to the sensing protein, or the analyte may be covalently linked to or non-covalently complexed with a ligand or binding partner which selectively binds to the sensing protein. Alternatively, the analyte may be covalently linked to or non-covalently complexed with another chemical species to together form a ligand or binding partner that selectively binds to the sensing protein. The sensing protein can, for example, be an antibody or antibody fragment.

In other specific embodiments, the sensing polysaccharide is a binding partner to which the analyte selectively binds. Alternatively, the sensing polysaccharide binds to a binding partner to which the analyte also binds. In these cases, the analyte may be a protein or other polypeptide, a ligand or binding partner which selectively binds to the sensing polysaccharide, or the analyte may be covalently linked to or non-covalently complexed with a protein or other polypeptide, ligand or binding partner which selectively binds to the sensing polysaccharide. Alternatively, the analyte may be covalently linked to or non-covalently complexed with another chemical species which together forms a ligand or binding partner that selectively binds to the sensing polysaccharide. The sensing polysaccharide can, for example, be a polymer of a monosaccharide analyte (e.g., a dextran for glucose detection.)

Further the analyte sensing compositions of this invention can be employed to detect analytes that inhibit or otherwise interfere with binding of the members of a binding pair (e.g., a ligand and its receptor). In this case, the sensing polymer (e.g., the sensing protein or sensing polysaccharide) is a polymer which functions as one member of the binding pair, the binding of which is inhibited by the analyte. Analyte sensing compositions for the detection and/or quantitation of an inhibitor of binding would also comprise the other member of the binding pair, present in an amount sufficient to not be limiting to binding (e.g., in the case of sensing protein which is a receptor, the other member of the binding pair is the ligand of that receptor). The analyte sensing compositions of this invention can thus be employed to screen for the presence of inhibitors of binding of a binding pair or binding partners. For example, the analyte sensing compositions of this invention in which the sensing protein is avidin could be employed to detect the presence of inhibitors, for example competitive binding inhibitors, of the binding of avidin to biotin.

In other specific embodiments, the sensing protein is an antibody or an antibody fragment which binds selectively or specifically to a particular antigen and the analyte is the antigen which binds directly to the antibody or antibody fragment or the analyte may be covalently linked to or non-covalently complexed with an antigen which selectively binds to the sensing protein. Alternatively, the analyte may be covalently linked to or non-covalently complexed with another chemical species which together form an antigen that selectively binds to the sensing protein antibody or antibody fragment. The antibodies and antibody fragments employed as sensing proteins may be obtained from commercial sources, isolated from natural sources, or obtained by recombinant methods.

In another specific embodiment, the analyte is an antibody or antibody fragment and the sensing protein is an antigen of the antibody or antibody fragment, containing an epitope which selectively binds to the antibody or antibody fragment, or the sensing protein is derivatized to display one or more antigens which selectively bind to the antibody or antibody fragment. More specifically, the sensing protein is covalently derivatized, prior to complexation with the carbon nanotube, to display one or more antigens which selectively bind to the antibody or antibody fragment. The presence and/or concentration of the antibody or antibody fragment in contact with the sensing composition is determined by detection of modulation in the optical properties of the carbon nanotube (e.g., fluorescence emission) as antibody or antibody fragments contacting the sensing solution bind to the antigens or epitopes of the sensing protein.

In specific embodiments, the analyte is a natural ligand of a receptor employed as the sensing protein. In specific embodiments, the analyte is not the natural ligand of the receptor, which may include chemical derivatives of the natural ligand, but nevertheless selectively binds to the receptor in specific embodiments, the receptor is obtained from commercial sources, is isolated from natural sources, or is prepared by recombinant methods. In specific embodiments, the receptor is a variant, derivative, or semi-synthetic analog of a naturally-occurring receptor which, for example, has been modified by modification of one or more amino acids to exhibit enhanced affinity or altered affinity for a selected ligand, is a deglycosylated form of a naturally-occurring receptor or a variant or derivative thereof, which retains function as a receptor for binding selectively to a ligand.

In another aspect, the invention provides materials and methods for detecting analytes by competitive binding assays. Most generally, in this embodiment, the analyte is a ligand or antigen to which a binding partner (e.g., a ligand receptor or antibody or antibody fragment) selectively binds. The analyte may also be a substrate which binds selectively or specifically to an enzyme. In one embodiment, the sensing composition for the competitive binding assay comprises carbon nanotubes non-covalently complexed with a sensing polymer, such as a protein or a non-ionic detergent, which is covalently derivatized, prior to complexation with the carbon nanotube, to display one or more ligands or antigens which selectively bind to the binding partner. In this embodiment the sensing composition further comprises the binding partner which is, at least in part, bound to the one or more Uganda or antigens covalently displayed on the sensing polymer. Free analyte coming into contact with the sensing composition, at a sufficient concentration, binds to the binding partner in the sensing composition, displacing, at least in part, binding partners, that were bound to the ligand or antigens covalently displayed on the sensing polymer. Displacement of the binding partner from the carbon nanotube/sensing polymer complex modulates the optical properties (e.g., fluorescence emission) of the carbon nanotube. Detection and analysis of the modulation allows detection of the analyte and/or measurement of the concentration of analyte in contact with the sensing composition. Standard methods of analysis used in competitive binding assays can be employed to determine analyte concentrations. The ligand or antigen covalently bound to the sensing polymer may be chemically identical to the analyte to be detected except that the ligand or antigen is covalently attached to the sensing polymer. Alternatively, the ligand or antigen covalently bound to the sensing polymer can be a chemical variant of the analyte (e.g., a polymer of the analyte or containing the analyte) which nevertheless binds to the binding partner. The analyte variant covalently bound to the sensing polymer can be selected to have binding affinity for the binding partner that is the same as or different from that of the analyte for the binding partner.

In a specific embodiment, the sensing polymer is a protein. In a specific embodiment, the sensing polymer is a polysaccharide. In a specific embodiment, the sensing polymer is an organic polymer that is not a protein, a nucleic acid or a carbohydrate. In another embodiment the sensing polymer is poly(ethylene glycol). In a specific embodiment useful in a competitive binding assay, the sensing polymer is poly(ethylene glycol) to which one or more analytes or analyte variants are covalently attached. In a more specific embodiment, for use in detection of a selected steroid, the sensing polymer is polyethylene glycol) to which one or more of the selected steroids or steroid variants are covalently attached. In a more specific embodiment, for use in detection of 17β-estradiol, the sensing polymer is poly (ethylene glycol) to which one or more 17β-estradiols or one or more 17β-estradiol variants are covalently attached. In another embodiment the sensing polymer is a polyoxyethylene sorbitan fatty acid ester, such as a monolaurate ester (such as Tween 20™). For use in this invention as a sensing polymer, polyoxyethylene sorbitan fatty acid esters can be functionalized with one, two, three or more (if functionalization sites are available) of the same chemical species (or moiety) that is selective for an analyte of interest. In a specific embodiment useful in a competitive binding assay, the sensing polymer is a polyoxyethylene sorbitan fatty acid ester to which one or more analytes or analyte variants are covalently attached. In a more specific embodiment, for use in detection of one member of a selected binding partner pair (e.g., avidin, strepavidin), the sensing polymer is a polyoxyethylene sorbitan fatty acid ester to which the other member of that binding partner pair (e.g., biotin) is covalently attached.

The semiconducting SWNT/sensing polymer complex is present in the analyte sensing composition in an amount sufficient to generate a luminescence response of sufficient intensity such that a modulation in that response resulting from the interaction of the analyte with the sensing polymer is detectible. Preferably, the semiconducting SWMT/sensing polymer complex is provided in an amount sufficient to allow detection of the analyte at a selected lower concentration limit. Preferably the analyte sensing composition does not contain any substantial amounts of carbon nanotubes which are not complexed with sensing polymer. Preferably, the analyte sensing composition does not contain any substantial amount of free sensing polymer that is not complexed with a carbon nanotube or other carbon nanostructured component of the sensing solution.

The analyte sensing solution may contain other functional components as needed in an amount sufficient to provide the desired sensing functionality. For example, the sensing solution may contain enzyme co-factors, co-reactants, oxidation agents or reducing agents as may be needed to facilitate selective reaction of the analyte mediated by the sensing protein enzyme. The analyte sensing solution may contain additional functional components, as needed and in an amount sufficient to provide the desired functionality, which facilitate ligand-receptor binding or antigen-antibody (or antibody fragment) binding.

The analyte sensing composition may comprise carbon nanotubes complexed with one or more chemically selective species which are dispersed in a solid or semi-solid matrix wherein the complexed carbon nanotubes exhibit luminescence and the solid or semi-solid matrix is selectively permeable to the analyte.

The invention also provides a sensor element for detecting an analyte which comprises:
 a selectively porous container for receiving and retaining the components of a sensing composition, and
 an analyte sensing composition, as described above, within the selectively porous container wherein the selectively porous container is sufficiently porous to allow the analyte to enter the container without allowing the functional components of the sensing solution to exit the container.

The sensor element can alternatively comprise an analyte sensing composition dispersed in a solid or semi-solid matrix wherein the solid or semi-solid matrix is selectively porous to the analyte.

The sensor element of the invention may be a tissue implantable sensor element. Tissue implantable sensor elements can be prepared employing biocompatible materials. Tissue implantable sensor elements can be encased in a biocompatible hydrogel matrix. The hydrogel matrix can contain one or more growth factors which induce vascularization in tissue in which the sensor element is implanted.

The invention also provided a sensing system for detecting the presence of an analyte or for determining the amount of an analyte which comprises:
 an analyte sensing composition comprising a semiconducting SWNT/complexed with one or more polymers including at least one sensing polymer, as described above,
 a source of electromagnetic radiation, e.g., light, for exciting luminescence of the SWNT/protein complex and
 a detector for detecting the luminescence response generated by the SWNT/sensing polymer complex on reaction of the analyte mediated by the sensing polymer or on binding of the analyte (directly or indirectly) to the sensing polymer.

In specific embodiments the sensing polymer is a sensing protein or a sensing polysaccharide. In specific embodiments the sensing polymer is a polymer other than a polynucleotide.

The analyte sensing solution is brought into contact with an environment (e.g., a liquid or solid sample, a biological fluid, an organism, a microorganism or medium containing microorganisms, an animal, a mammal, a human, a cell growth medium, etc.) such that analytes that may be in the environment can enter into and interact with the sensing composition and the sensing polymer therein to modulate the luminescence response of the SWNT/sensing polymer complex.

In a specific embodiment, the sensing composition is retained in a selectively porous sensing element which can be placed in contact with an environment which may contain the analyte. The selectively porous sensing element is sufficiently porous to allow the analyte to enter the sensing element without allowing any substantial release of functional components of the sensing composition. In a specific embodiment, the environment which the sensor element contacts is a tissue or body fluid. In a specific embodiment, the sensing element is inserted into the body or a body part of an animal, including any mammal and including a human.

In a more specific embodiment, the analyte is glucose and the sensing polymer is glucose oxidase. In a yet more specific embodiment, the analyte is glucose, the sensing protein is glucose oxidase and the mediator is ferricyanate. In another embodiment, the analyte is glucose and the sensing polymer is a dextran and the sensing composition further comprises a sensing partner which is a glucose binding partner, and which more specifically is concanavalin A or apo-glucose oxidase.

In another aspect, the invention provides a method for preparing a carbon nanotube complex with a polymer which comprises the steps:
 a. providing surfactant dispersed carbon nanotubes;
 b. contacting the surfactant dispersed carbon nanotubes with the polymer to form a mixture
 c. dialyzing the mixture to remove the surfactant such that carbon nanotube complexes with the polymer are formed.

In specific embodiments the polymer is a biological polymer such as a protein or other polypeptide or a polysaccharide.

In preferred methods, the polymer is a protein, including a soluble protein (typically soluble in aqueous media) or an amphiphilic protein, and the surfactant is non-denaturing. The surfactant is a surfactant that can be removed by dialysis and is typically not a polymeric surfactant. The surfactant can, among others be an anionic surfactant, such as a cholate, a nonionic surfactant or a zwitterionic surfactant that is not polymeric. In preferred embodiments, the relative amounts of polymer and carbon nanotube in the mixture that is to be dialyzed is selected to maximized the formation of carbon nanotube/polymer complexes and minimize the amount of free-polymer in the mixture after dialysis. Preferably the relative amount of carbon nanotube to polymer in the mixture is selected to obtain a monolayer or less of the polymer (including protein) on the carbon nanotube.

The methods of this invention can also be employed when the protein or other polymer is not soluble in an aqueous medium, for example when the protein is a membrane protein. In this case, the protein or other polymer may be initially dispersed with a surfactant (or mixture of surfactants) which does not denature the protein or otherwise detrimentally affect the polymer, as is known in the art, the dispersed protein or other polymer is then contacted with the dispersed carbon nanotubes and the surfactant(s) are thereafter removed from the system to form the carbon nanotube/protein complex.

Dialysis is performed as is known in the art using surfactant-free medium (aqueous medium) to remove surfactant without significant loss of carbon nanotubes or polymer, and to retain any function of the polymer. More specifically, the dialysis is performed under conditions selected to retain the biological function of a protein to be complexed with a carbon nanotube.

BRIEF DESCRIPTION OF THE DRAWINGS

FIG. 1A is a graph of normalized fluorescence intensity of semiconducting SWNTs during equilibrium dialysis of a SWNT/cholate suspension with added glucose oxidase to form SWNT/glucose oxidase complexes. Fluorescence of semiconducting SWNTs is measured using transient fluorescent spectroscopy with 785 nm excitation. Fluorescence intensity is normalized to the Raman tangential mode at 1592 cm$^{-1}$ as a function of dialysis time. Normalized fluorescence intensity decreases as cholate is removed. A phase change, indicated by a sharp drop in normalized fluorescence intensity, occurs at about 3.8 hrs after the start of dialysis, where surface assembly occurs. FIG. 1B provides a comparison of the emission spectrum observed at the start of dialysis (t=0 hrs) from individual dispersed semiconducting SWNTs in a SWNT/cholate dispersion and the emission spectrum observed after macromolecular complex formation, here, SWNT/glucose oxidase complex formation. The emission spectrum shifts by about 10 meV and fluorescence intensity is reduced by a factor of 2.2. This shift is believed to be the result of increased polarity at the nanotube surface due to water penetration through cavities in the adsorbed enzyme layer shifts. FIG. 1C. The assembly event is concerted, as measured using the emission peak center, and occurs over an extremely narrow range of cholate concentrations as show in this graph of peak shift as a function of time.

FIGS. 2A-C: Non-covalent functionalization of the nanotube surface. Illustrating the effect of ferricyanide ion at the nanotube surface. FIG. 2A. Through gaps between macromolecules on the nanotube surface, the mediator can interact directly with the nanotube surface and allow the surface chemistry of an individual nanotube to be probed without an intervening surfactant layer. FIG. 2B. Electroactive species, such as ferricyanide ion exemplified herein, can withdraw electronic density from the nanotube valence bands, and remain bonded to the nanotube in the absence of a covalent bond. Both the ferricyanide (shown) and ferrocyanide ions react in this way, withdrawing electron density from the nanotube with increasing surface coverage. FIG. 2C. The process of withdrawal of electron density is tracked using SWNT fluorescence, scaled by the initial emission intensity $I_o$ which trace single and dual site binding isotherms for ferricyanide and ferrocyanide ions, respectively.

FIG. 4A. A micro-dialysis capillary 100 (MWCO=13 kDa) is loaded with the functionalized nanotubes (GOx-SWNT-Fe $(CN)_6^{-3}$) in solution allowing glucose to diffuse through the dialysis membrane (101) with containment of the sensing medium. The micro-dialysis capillary may be inserted into tissue, for example at a finger tip as illustrated. FIG. 4B is a graph which shows the effect of injection of 62.5 mM of ferricyanide into a suspension containing semiconducting SWNT/GOx. A rapid diminution in the scaled near-IR fluorescence occurs due to the interaction of the ferricyanide with the SWNT. The response is normalized by the pristine $I_a$ and fully reacted $I_b$ emission. Subsequent addition of 1.4 mM, 2.4 mM, and 4.2 mM of glucose, as indicated, causes a quantitative restoration of the fluorescence. The sensing medium exhibited a detection limit of 34.4 µM and response time less than 80 s. FIG. 4C is a graph of SWNT fluorescence response as a function of glucose concentration. The response function relates the normalized intensity to the local glucose concentration.

FIG. 9A Fluorescence of 2% cholate suspended SWNT on addition of glucose. FIG. 9B. Fluorescence of GOx-SWNT on addition of glucose. Mediator, ferricyanide ion, was not added to either of these controls. The control samples were both buffered (pH 7.4) and maintained at 37 C. No significant change in fluorescence was observed on glucose addition in these control experiments.

FIG. 14 B is a scheme showing the mechanism of action of a glucose sensor employing a SWNT/dextran complex and based on competitive binding of a protein (having binding affinity for glucose and dextran, e.g., conA or apo-GOx). Binding of glucose to the protein causes SWNT fluorescence attenuation.

FIG. 15 is a schematic illustration of a sensing system of this invention in which a sensing composition is introduced into a sensing element (e.g., a capillary porous to analyte but not to sensing components). The system has a light source for exciting luminescence of the carbon nanotube and a detector for detecting that luminescence and changes in the luminescence.

DETAILED DESCRIPTION OF THE INVENTION

Figure 1A:
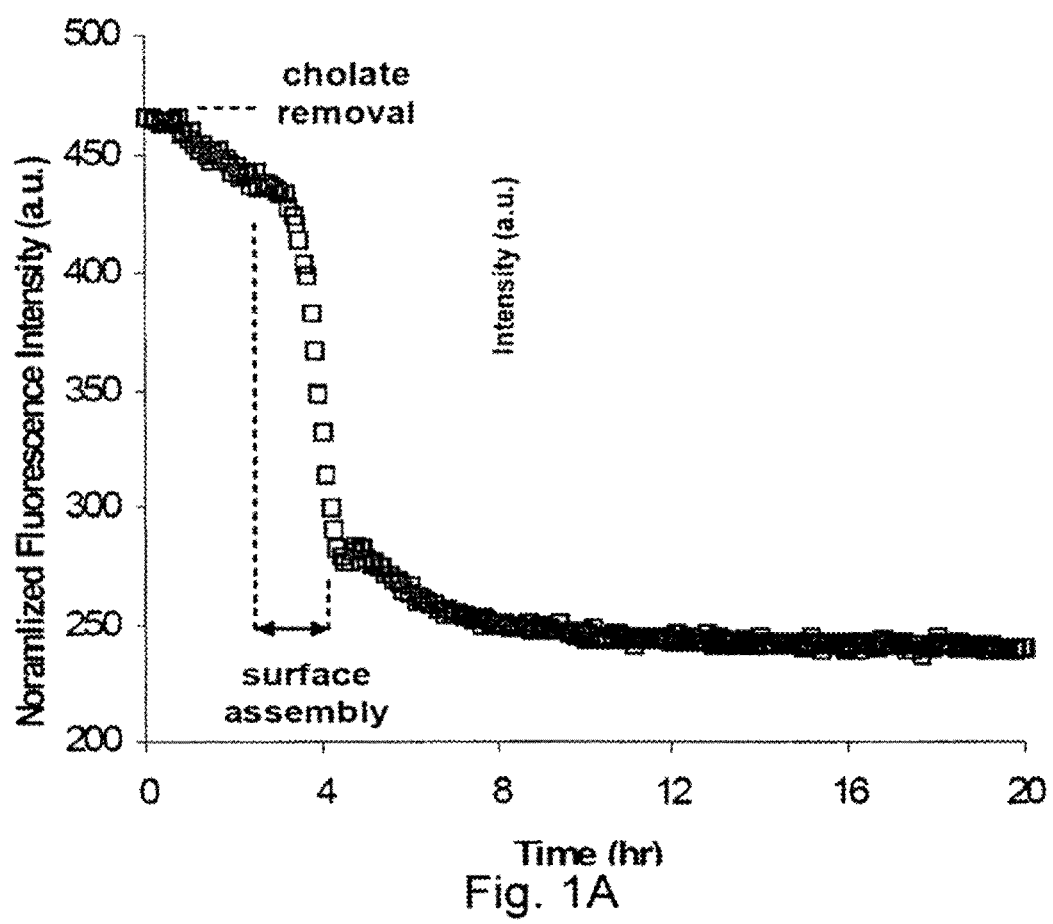
FIGS. 1A-C.

The invention relates most generally to non-covalent complexes of carbon nanotubes with polymers, particularly sensing polymers and more particularly with proteins, polypeptides and polysaccharides.

The present invention provides sensors which comprise analyte sensing composition which in turn comprise complexes of carbon nanotubes with sensing polymers. In these complexes, the sensing polymer is non-covalently complexed with the carbon nanotube. Preferably, in the sensing composition, the sensing polymer is complexed with the carbon nanotube to provide individually dispersed carbon nanotubes with no electronic interaction or minimal electronic interaction with other carbon nanotubes in the composition. The sensing polymer provides for selective interaction with an analyte or specific interaction with an analyte. The term "specific" is used to indicate an interaction that can be used to distinguish the analyte from most other chemical species except optical isomers, isotopic variants (i.e., where one or more atoms are enriched in a given isotope, e.g., deuterated species) and perhaps certain isomers. The term "selective" is used to indicate an interaction that is sufficiently specific that it can be used to distinguish the analyte in practice from other chemical species in the system in which the sensor and sensing composition is to be employed. The term "selective binding" is thus used to refer to a protein, other polymer or other chemical species that binds to a limited set of other chemical species (usually species that are related in chemical structure). Enzymes, antibodies (and antibody fragments) and receptors, among other proteins, exhibit selective binding which may in some cases be specific. Other polymers, such as polysaccharides may functions as ligands (e.g., for binding to a protein) or as a member of a binding pair. In the methods and devices of this invention "selective binding" can provide the selectivity needed to detect a selected analyte (or relatively small group of related analytes) in a complex mixture, e.g., in a biological fluid or tissue. For example, selective binding of a substrate to an enzyme can provide the desired level of selectivity needed to detect a selected analyte (which is the enzyme substrate). Selective binding includes "specific binding" which is intended to indicate more limited binding which can be used to distinguish a binding partner from most other chemical species except optical isomers, isotopic variants and perhaps certain structural isomers. Sensing polymers of this invention can be selected to provide selective or specific interactions with one or more analytes (preferably one analyte).

The term analyte is used generally herein to refer to any chemical species which is to be detected or the quantity of which is to be determined. Analytes include small molecules, such as sugars, steroids, antigens and polymeric species such as proteins (e.g., enzymes, antibodies, antigens). In specific embodiments, analytes are one member of a binding partner pair. In specific embodiments analytes are monosaccharides. In a specific embodiment the analyte is glucose. Methods, devices and compositions herein are particularly well suited to the detection and quantitation of analytes in solutions, such as in biological fluids. Methods, device and compositions herein are also particularly well suited to the detection and quantitation of analytes in biological tissues.

The sensing polymer may be formed by derivatization of a polymer, e.g., poly(ethylene glycol), with one or more chemically selective species which provide for selective or specific interaction with one or more analytes. Additional polymers that may be derivatized to form sensing polymers include among others, polyvinyl alcohol), poly(vinyl chloride), (e.g., and copolymers thereof), polysorbitan esters (e.g., polyoxyethylene sorbitan fatty acid esters.) Each sensing polymer may be derivatized to carry one, two or more chemically selective species or moieties which are selective for the same analyte. A sensing polymer may be derivatized to carry one, two or more chemically selective species or moieties which are selective for the same or different analyte. Thus a single, carbon nanotube/sensing polymer complex may be responsive to one, two or more analytes. In specific embodiments, a sensing polymer contains one covalently bound chemically selective species or moiety which is selective for a single analyte of interest. The use of polymers which carry one such selective chemical species or moiety may be beneficial to prevent aggregation of carbon nanotube/sensing polymer complexes. Such aggregation may be detrimental in analyte sensing applications. The chemically selective species or moiety may be directly bonded to the polymer or indirectly bonded through a linker group.

The sensing polymer may be a sensing protein or a sensing polysaccharide. A sensing protein has function for selective interaction (or specific interaction) with an analyte. The sensing protein may be a naturally-occurring protein or recombinant protein that exhibits as a consequence of its protein structure a selective interaction with an analyte. The sensing protein can interact directly with an analyte (e.g., by binding or reaction) or can interact indirectly with the analyte by interaction (e.g., by binding or reaction) with another chemical species which in turn interacts with the analyte. The sensing protein may be formed by chemical derivatization of a protein that does not exhibit any selective interaction with an analyte. For example, the sensing protein may be formed from a protein that is derivatized covalently to carry one or more chemically selective species (or moieties) which individually or collectively provide for selective interaction with one or more analytes. Proteins may be derivatized at one or more termini or at one or more amino acid side changes (e.g., those of lysine, glutamine, arginine, serine, aspartate, glutamate, etc.) to provide for chemical selectivity. Proteins useful as sensing proteins include those which are derivatized at one or more termini and/or one or more amino acid side chains to carry one or more steroids or steroid derivatives.

A sensing polysaccharide has function for selective interaction (or specific interaction with) analyte. The sensing polysaccharide may be naturally-occurring, for example isolated from nature, chemically-derivatized, chemically-modified or chemically-synthesized. The sensing polysaccharide can interact directly with an analyte (e.g., by binding or reaction) or can interact indirectly with the analyte by interaction (e.g., by binding or reaction) with another chemical species which in turn interacts with the analyte. The specific structure of the polysaccharide or the presence of a specific monosaccharide may facilitate a selective interaction with an analyte. The sensing polysaccharide may be formed by chemical derivatization or modification of a polysaccharide that does not exhibit any selective interaction with an analyte. For example, the sensing polysaccharide may be formed from a polysaccharide that is derivatized covalently to carry one or more chemically selective species (or moieties) which individually or collectively provide for selective interaction with one or more analytes. Polysaccharides may be derivatized at any available location of the polymer that is reactive to provide for chemical selectivity. Polysaccharides that are useful, for example, as sensing polymers include those polysaccharides which bind to a binding partner, for example a protein, that also binds to a monosaccharide analyte. Polysaccharides include those having 10 or more saccharide monomers. Polysaccharides include those having 20 or more saccharide monomers Carbon nanotubes are carbon nano structures in the form of tubes, ranging in general in diameter from about 0.5-200 nm, (more typically for single-walled carbon nanotubes from about 0.5-5 nm) The aspect ratio of nanotube length to nanotube diameter is greater than 5, ranges from 10-2000 and more typically 10-100. Carbon nanotubes may be single-walled nanotubes (a single tube) or multi-walled comprising with one or more smaller diameter tubes within larger diameter tubes. Carbon nanotubes are available from various sources, including commercial sources, or synthesis employing, among others, arc discharge, laser vaporization, the high pressure carbon monoxide processes.

The following references provide exemplary methods for synthesis of carbon nanotubes: U.S. Pat. No. 6,183,714; PCT/US99/25702; PCT/US99?21367; A. Thess et al. Science (1996) 273:483; C. Journet et al. Nature (1997) 388, 756; P. Nikolaev et al. Chem. Phys. Lett. (1999) 313:91; J. Kong et al Chem. Phys. Lett. (1998) 292: 567; J. Kong et al. Nature (1998) 395:878; A. Cassell et al. J. Phys. Chem. (1999) 103:6484; H. Dai et al. J. Phys. Chem. (1999) 103:11246; Bronikowski, M. J., et al., Gas-phase production of carbon single-walled nanotubes from carbon monoxide via the HiPco process: a parametric study. J. Vac. Sci. Tech. A, 2001. 19(4): p. 1800-1804; Y. Li et al. (2001) Chem. Mater. 13:1008; N. Franklin and H. Dai (2000) Adv. Mater. (2000) 12:890; A. Cassell et al. J. Am. Chem. Soc. (1999) 121:7975; International Patent Application WO 00/26138. International Patent Applications WO 03/084869 and WO 02/16257 also provide an overview of synthetic methods for the preparation of single-walled carbon nanotubes as well as methods for purification of carbon nanotubes and the removal of catalyst and amorphous carbon.

Carbon nanotubes produced in such methods are typically poly-disperse samples containing metallic and semi-conducting types, with characteristic distributions of diameters [28].

A method for separating single-walled carbon nanotubes by diameter and conformation based on electronic and optical properties has been reported (Smalley et al. International Patent Application WO 03/084869. The method can be employed to prepare carbon nanotube preparations having enhanced amounts of certain single walled carbon nanotube types. Narrow (n, m)-distributions of single-walled carbon nanotubes are reported using a silica-supported Co—Mo catalyst [30]. M. Zheng et al. Science (2003) 302 (November) 1545 report nanotube separation by anion exchange chromatography of carbon nanotubes wrapped with single-stranded DNA. Early fractions are reported to be enriched in smaller diameter and metallic nanotubes, while later fractions are enriched in larger diameter and semiconducting nanotubes.

Carbon nanotube compositions generally useful in sensors of this invention are those which exhibit optical properties which are sensitive to the environment of the nanotube, i.e., optical properties which can be modulated by changes in the environment of the nanotube. More specifically, carbon nanotube compositions useful in sensors of this invention comprise semiconducting SWNTs which can exhibit luminescence, and more specifically which exhibit photo-induced band gap fluorescence. Carbon nanotube compositions which exhibit luminescence comprise SWNTs which when electronically isolated from other carbon nanotubes exhibit luminescence, including fluorescence and particularly those which exhibit fluorescence in the near-IR. Carbon nanotube compositions of this invention comprise individually dispersed semiconducting SWNTs exhibiting luminescence, particularly photo-induced band gap fluorescence. Carbon nanotube compositions of this invention may also include MWNT and other carbon nanomaterials as well as amorphous carbon. Preferably carbon nanotube compositions of the invention comprise a substantial amount of semiconducting SWNTs, e.g., 25% or more by weight of such SWNTs. More preferably the carbon nanotube compositions of this invention comprise a predominance of semiconducting SWNTs (i.e., 50% or more by weight of semiconducting SWNTs). In general, carbon nanotube compositions will contain a mixture of semiconducting SWNTs of different sizes which exhibit fluorescence at different wavelengths.

Single walled carbon nanotubes are sheets of graphene single layer of graphite—rolled into a molecular cylinder [25] and indexed by a vector connecting two points on the hexagonal lattice that conceptually forms the tubule with a given "chiral" twist [1, 2, 28]. Hence, (nm) nanotubes are those formed by connecting the hexagon (as shown in the cited references) with one n units across and m units down (n>m by convention.) Carbon nanotubes have a fascinating relationship between geometric and electronic structure: the 1-D nature of the nanotube exerts a unique quantization the circumferential wave-vector and hence, simple perturbations of this chirality vector yield enormous changes in molecular properties [25], [26]. When $|n-m|=0$, the system is truly metallic in nature while if $|n-m|=3q$ (with q a nonzero integer) the nanotube possesses a small curvature induced gap and if $|n-m|\neq 3q$ then the system is semiconducting with a measurable band-gap.

The sensing composition optionally contains SWNTs that are not semiconducting, i.e. metallic SWNTs, that are complexed with one or more proteins or other polymers, SWNTs (semiconducting or metallic) that are fully or partially complexed with proteins and/or polymers and/or surfactants, other carbon nanotubes or other carbon nanostructured materials that are complexed with protein (which may or may not be sensing proteins), polymers (which may or may not be sensing polymer) and/or surfactant, as well as aggregates, including ropes, of SWNTs, or aggregates of other carbon nanotubes or nanostrutured materials. The sensing composition may further contain amorphous carbon and other byproducts of carbon nanotube synthesis, such as residual catalyst. Preferably, the types and levels of any of these optional components is sufficiently low to minimize detrimental affect on the function of the sensing solution.

An electroactive species most generally is a species, e.g., a molecule, complex or polymer, that can function for transport of electrons or holes, e.g., can function for electron transfer.

A redox mediator is an electron transfer agent which functions for carrying electrons between a chemical species and an electrode or between two chemical species. More specifically a redox mediator is a substance (or substances) that facilitates the flow of electrons in a reduction-oxidation reaction. In certain methods and devices of this invention the redox mediator functions to carry electrons from an analyte or a reaction product of an analyte to a carbon nanotube. Electron transport between the carbon nanotube and the analyte or its reaction product modulates the optical properties of the carbon nanotube which can be employed to detect analyte or the generation of reaction products from the analyte.

In general any organic or organometallic redox species can be used as a redox mediator in this invention. More than one redox mediator may be involved in the electron transport from the analyte to the carbon nanotube. Redox mediators include among others transition metal compounds or complexes, for example, compounds or complexes of osmium, ruthenium, iron, iridium, vanadium, and cobalt. Redox mediators, more specifically include, metal complexes, particularly transition metal complexes, particularly metal complexes of osmium, ruthenium, iron, iridium, vanadium, copper, aluminum and cobalt, having one or more ligands which are halogens (e.g., Cl), OH, groups, CN groups (cyano groups), N-containing heterocycles (e.g., pyridine and/or imidazole or derivatives thereof, metalocenes or derivatives thereof, including ferrocene, nickelocene, etc. and derivatives thereof (e.g., dimethylferrocene, decamethylferrocene, etc.)). Redox mediators include among others ferricyanide, ferrocyanide, $Cr(OH)_3$, $Al(III)(OH)_3$, and $Cu(II)_2Fe(II)(CN)_6$. Organic redox species useful as redox mediators include among others, organic dyes (e.g., viologens or substituted viologens (e.g., methylviologen), phthalocyanines, quinones (e.g., naphthoquinone, phenoquinone, benzoquinone, naphthenequinone, and the like including derivatives thereof), electroactive polymers (such as polypyroles or derivatized polypyroles), tetrathiafulvalene (TTF) and derivatives thereof, dopamine and derivative thereof, epinephrine and norepinephrine and derivatives thereof, tetracyanoquinodimethane (TCNQ) and derivatives thereof, phenazine methosulfate or phenazine ethosulfate and derivatives thereof. Exemplary redox mediators for use with specific enzymes are provided in U.S. Pat. No. 5,413,690, which is incorporated by reference herein, at least in part, for a description of such redox mediators.

Carbon nanotube/polymer complexes of this invention can be made by initial formation of individually dispersed carbon nanotubes. Individually dispersed nanotubes are formed essentially as previously described (10) by dispersion of carbon nanotube product in aqueous surfactant solution employing high-sheer mixing and sonication to disperse the nanotubes in surfactant, followed by centrifugation to aggregate bundles or ropes of nanotubes and decanting of the upper 75-80% of supernatant to obtain micelle-suspended carbon nanotube solutions or dispersions (20-25 mg/L). Surfactant-dispersed carbon nanotubes are contacted with polymer solutions, preferably aqueous solutions of polymer, and subjected to dialysis under conditions in which the surfactant is removed without removal of the polymer or carbon nanotube. As surfactant is removed by dialysis, carbon nanotube/polymer complexes are formed.

The amount and type of surfactant employed for dispersion of carbon nanotubes can be readily determined employing methods that are well-known in the art. As noted in detail below, the surfactant employed must be compatible with the components of the sensing compositions, particularly with the sensing polymer, specifically with the sensing protein. The surfactant must not destroy the function of the sensing polymer or sensing protein. In certain cases, the surfactant must be a non-denaturing surfactant that does not significantly detrimentally affect the function (e.g., binding or enzymatic function) of the protein or other polymer. The amount of surfactant needed to disperse the carbon nanotubes can be determined by routine experimentation. It is preferred to employ the minimum amount of surfactant needed to provide individually dispersed carbon nanotubes. Surfactants are typically employed between about 0.1% to about 10% by weight. (more typically from 0.5% to 5% by weight) in aqueous solution to disperse carbon nanotubes.

For the formation of carbon nanotube/protein complexes, the surfactant originally employed (1% by weight in water) sodium dodecylsulfate (SDS) to form the individually dispersed carbon nanotubes is replaced with a non-denaturing surfactant, e.g., sodium cholate (2% by weight in water). Surfactant-dispersed carbon nanotubes are contacted in aqueous solution with functional protein or other polymer and subjected to dialysis under conditions in which the surfactant is removed without removal of the protein or carbon nanotube and the protein retains function. As surfactant is removed by dialysis, carbon nanotube/protein complexes are formed. The surfactant employed is of sufficiently low molecular weight to be removed by dialysis while the polymer is not.

Complexes of carbon nanotubes with chemically selective polymers (sensing polymers) can be prepared by methods other than the dialysis method specifically described herein. In some cases, the polymer may be complexed with the nanotube simply by contacting the nanotube with a sufficient amount of polymer and apply vigorous mixing (e.g., sonication), if necessary to obtain dispersed nanotubes. In other cases, an already dispersed nanotube composition comprising surfactant or polymer which functions for dispersion of the nanotube may be contacted with a sufficient amount of the sensing polymer and if necessary apply vigorous mixing to displace at least a portion of the surfactant or polymer already associated with the nanotube.

The preparation of surfactant dispersed carbon nanotubes employs vigorous mixing, for example high shear mixing, which may be provided using a high speed mixer, a homogenizer, a microfluidizer or other analogous mixing methods known in the art. Sonication, including various ultrasonication methods can be employed for dispersion. Preferred methods for dispersion involve a combination of high sheer mixing and sonication.

International Patent Application WO 03/050332 reports the preparation of stable carbon nanotube dispersions in liquids. International Patent Application WO 02/095099 reports noncovalent sidewall functionalization of carbon nanotubes.

In specific embodiments, analyte sensing compositions of this invention comprise one or more carbon nanotube/protein complexes. In these complexes, one or more protein molecules are non-covalently associated with the carbon nanotube. Preferably, the protein molecule or molecules complexed with the carbon nanotube provide monolayer coverage or less of the carbon nanotube by protein.

In preferred carbon nanotube/protein complexes of this invention, the complexed protein retains its biological function and the complexed carbon nanotube is a semi-conducting carbon nanotube which exhibits band gap fluorescence.

In specific embodiments, analyte sensing compositions of this invention comprise one or more carbon nanotube/polysaccharide complexes. In these complexes, one or more polysaccharide molecules are non-covalently associated with the carbon nanotube. Preferably, the polysaccharide molecule or molecules complexed with the carbon nanotube provide monolayer coverage or less of the carbon nanotube by protein.

In preferred carbon nanotube/polysaccharide complexes of this invention, the complexed polysaccharide retains its biological function and the complexed carbon nanotube is a semi-conducting carbon nanotube which exhibits band gap fluorescence.

Surfactants preferred for use in the methods herein are non-denaturing and can be removed by dialysis (i.e., are dialyzable). Non-denaturing surfactants include anionic surfactants, non-ionic surfactants and zwitterionic (or amphoteric) surfactants. The term denature (or denaturing) is used herein with respect to protein structure and function. A denatured protein has lost its functional structure. Contact with surfactants, as well as other environmental changes (e.g., temperature or pH changes), can cause structural changes in proteins, and these structural changes can affect one or more of the biological functions of the protein. For example, a denatured enzyme will no longer exhibit enzymatic function. Contact with a non-denaturing surfactant does not have any significant detrimental affect on one or more of the biological functions of a given protein. Denaturing can affect enzymatic activity, protein binding interactions and other biological functions of a protein. A normally denaturing surfactant may function as a non-denaturing surfactant over a selected concentration range or with respect to certain proteins which are more resistant to its denaturing effect than most other proteins.

Non-denaturing surfactants include, among others, bile acids and derivatives of bile acids, e.g., cholate (salts of cholic acid, particularly sodium cholate), deoxycholate (salts of deoxycholic acid, particularly sodium deoxycholate), sulfobetaine derivatives of cholic acid, particularly 3-[(3-cholamidopropyl)dimethylamrnonio]-1-propanesulfonate (CHAPS); carbohydrate-based surfactants, for example, alkyl glucosides, particularly n-alkyl-β-glucosides (more specifically, n-octyl-α-glucoside (OG)), alkyl thioglucosides, particularly n-alkyl-β-thioglucosides (more specifically, n-octyl-β-thioglucoside (OTG)); alkyl maltosides, particularly n-alkyl-β-maltosides (more specifically, n-dodecyl-β-glucoside); alkyl dimethyl amine oxides (e.g., (C6-C14) alkyldimethyl amine oxides, particularly lauryldimethyl amine oxide), non-ionic polyoxyethylene surfactants, e.g., Triton™ X-100 (or octyl phenol ethoxylate), Lubrol™ PX, Chemal LA-9 (polyoxyethylene(9)lauryl alcohol); and glycidols, e.g., p-sonomylphenoxypoly(glycidol) (Surfactant 10G). A normally non-denaturing surfactant may function as a denaturing surfactant over a selected concentration range or with respect to certain proteins which are more sensitive to its denaturing effect than most other proteins.

Non-denaturing surfactant can also include mixtures of non-denaturing surfactants with denaturing surfactant where the amount of denaturing surfactant is sufficiently low in the mixture to avoid detrimental effect on the protein. Denaturing of a protein by a given surfactant is dependent upon the concentration of surfactant in contact with the protein and may also depend upon other environmental conditions (temperature, pH, ionic strength, etc.) to which the protein is being subjected. The denaturing effects of a selected surfactant, at selected concentrations, upon a selected protein can be readily assessed by methods that are well-known in the art.

Surfactants preferred for use in the preparation of carbon nanotube complexes of this invention are dialyzable, i.e., capable of being selectively removed form a surfactant dispersed carbon nanotubes by dialysis without significant removal of carbon nanotubes or the polymers that are to be complexed with the carbon nanotubes. Dialyzable, non-denaturing surfactants include, among others, bile acids and derivatives of bile acids, e.g., cholate (salts of cholic acid, particularly sodium cholate), deoxycholate (salts of deoxycholic acid, particularly sodium deoxycholate), sulfobetaine derivatives of cholic acid, particularly 3-[(3-cholamidopropyl)dimethylammonio]-1-propanesulfonate (CHAPS): carbohydrate-based surfactants, for example, alkyl glucosides, (e.g., C6-C14 alkyl glucosides), particularly n-alkyl-β-glucosides (more specifically, n-octyl-ᴣ-glucoside (OG)), alkyl thioglucosides, (e.g., C6-C14 alkyl thioglucosides), particularly n-alkyl-β-thioglucosides (more specifically, n-octyl-β-thioglucoside (OTG)); alkyl maltosides, (e.g., C6-C14 alkyl maltosides), particularly n-alkyl-ᴣ-maltosides (more specifically, n-dodecyl-β-glucoside); and alkyl dimethyl amine oxides (e.g., (C6-C14) alkyldimethyl amine oxides, particularly lauryldimethyl amine oxide). Dialyzable, non-denaturing surfactants for use in a given application with a given protein can be readily identified employing well-known methods.

The term protein is used herein as broadly as it is in the art to refer to molecules comprising of one or more polypeptide chains which may be linked to each other by one or more disulfide bonds. Proteins include glycoproteins (proteins inked to one or more carbohydrates), lipoproteins (proteins linked to one or more lipids), metalloproteins (proteins linked to one or more metal ions) and nucleoproteins (proteins linked to one or more nucleic acids). The term protein is however intended to exclude small peptides, such as those having less than 50 amino acids. The term protein includes polypeptides having 50 or more amino acids. A protein may comprise one or more subunits and the subunits may be the same or different. For example, a protein may be a homodimer (having two subunits that are the same) or a heterodimer (having two subunits that are different). Proteins typically have one or more biological functions. Proteins include enzymes which catalyze reactions and antibodies, transport proteins, receptor proteins or other proteins which bind to other chemical species (peptides, nucleic acids, carbohydrates, lipids, other proteins, antigens, haptens, etc.). Proteins useful in this invention include soluble proteins, membrane proteins and transmembrane proteins. Soluble proteins are of particular interest for the formation of carbon nanotube/protein complexes.

The term polypeptide is used to refer to peptides having 20 or more amino acids and in particular is not intended to refer to peptides such as those reported in WO 03/102020.

Proteins useful in this invention include those that exhibit selective (or specific) binding to given chemical species or, which are one member of a set (particularly a pair) of binding partners (e.g., avidin and biotin, a receptor and a receptor ligand, or an antibody or antibody fragment and an antigen to which it binds). In specific embodiments, useful proteins include soluble receptors and cell surface receptors. In other specific embodiments, useful proteins include G-protein coupled receptors (GPCRs). In more specific embodiments, useful proteins include steroid receptors, particularly estrogen receptors.

G-protein coupled receptors (GPCRs) are an important and diverse class of pharmaceutical targets in mammalian cellular membranes where they function as signal transducing elements, bind several classes of bioactive ligands and transmit information to the intracellular machinery.

In specific embodiments, proteins useful in this invention may contain one or more of the carbon nanotube binding sequences disclosed in International Patent Application WO03/102020. In another specific embodiment proteins useful in this invention do not contain any one or more of the carbon nanotube binding sequences disclosed in International Patent. Application WO03/102020.

There may be proteins which on complexation with semi-conducting carbon nanotubes form individually dispersed carbon nanotube complexes, but which do not exhibit band gap fluorescence. In these cases, the protein may itself quench the fluorescence or bind to a species which quenches the fluorescence. It has been determined experimentally that serum albumin (specifically bovine serum albumin, BSA) forms complexes with semi-conducting carbon nanotubes which do not exhibit band gap fluorescence. It is currently believed that BSA quenches the band gap fluorescence of the carbon nanotube. In a specific embodiment, proteins of this invention exclude serum albumin, particularly bovine serum albumin.

There may be proteins, particularly those which tend to self-aggregate or aggregate with other protein, which may on complexation with carbon nanotubes form complexes which exhibit band gap fluorescence, but in which the fluorescence is not sensitive to the environment of the carbon nanotube complex. It is currently believed that in such cases, multiple layers (i.e., more than a monolayer) of protein are formed on the carbon nanotube. The protein can then function to block access to or shield the carbon nanotube from the environment. Aggregation of proteins complexed with carbon nanotubes may force the aggregated complexes out of solution limiting access of analytes to the carbon nanotube. It has been found that concanavalin A, a lectin, forms complexes with semi-conducting carbon nanotubes which exhibit band gap fluorescence. However, the carbon nanotube/concanavalin A complexes aggregate and fluorescence of the complexed carbon nanotube is not sensitive to the environment of the carbon nanotube. In a specific embodiment, proteins of this invention for forming complexes with carbon nanotubes exclude concanavalin A. In another specific embodiment, proteins of this invention for forming complexes with carbon nanotubes exclude lectins.

Enzymes function by binding to a substrate and catalyze a reaction of the substrate. Substrate selectivity or specificity of an enzyme is, at least in part, determined by the selectivity or specificity with which the enzyme binds to a substrate. Enzymes include among others those that catalyze oxidation and/or reduction reactions and those that catalyze cleavage of certain bonds or the formation of certain bonds. It is understood in the art that enzyme function may require the presence of cofactors and/or co-enzymes. Further, it is understood in the art that enzyme function may be affected by pH, ionic strength, temperature or the presence of inhibitors. Methods and devices of this invention typically employ enzymes which are well-known in the art so that the requirements for any co-factors and/or co-enzymes and the effect of pH, ionic strength, temperature and other environmental factors a well as potential inhibitors will also be well-known.

Enzymes useful in analyte sensing composition of this invention include oxidases, dehyrogenases, esterases, oxigenases, lipases, and kinases, among others which may be obtained from various sources. More specifically, enzymes useful in analyte sensing compositions include glucose oxidases, glucose dehydrogenases, galactose oxidases, glutamate oxidases, L-amino acid oxidases, D-amino acid oxidases, cholesterol oxidases, cholesterol esterases, choline oxidases, lipoxigenases, lipoprotein lipases, glycerol kinases, glycerol-3-phosphate oxidases, lactate oxidases, lactate dehydrogenases, pyruvate oxidases, alcohol oxidases, bilirubin oxidases, sarcosine oxidases, uricases, and xanthine oxidases and wherein the analyte is a substrate for the enzyme.

Proteins, including enzymes, useful in this invention can be obtained from various sources, for example, from various commercial sources, through isolation by known methods from natural sources; through recombinant methods which are known in the art and by synthetic or semi-synthetic methods.

Proteins useful in this invention may be truncations, variants, derivatives, or semi-synthetic analogs of a naturally-occurring protein which, for example, has been modified by modification of one or more amino acids to exhibit altered biological function, e.g., altered binding, compared to the naturally-occurring protein, is a deglycosylated form of a naturally-occurring protein or a variant or derivative thereof, or has glycosylation different than that of a naturally-occurring protein. Proteins as well as protein truncations, variants; fusions, derivatives or semi-synthetic analogs of naturally-occurring proteins and enzymes useful in this invention exhibit a biological function that can be used detect an analyte. Protein truncations, variants, fusions, derivatives or semi-synthetic analogs of naturally-occurring proteins and enzymes may exhibit altered binding affinity and/or altered biological function compared to naturally-occurring forms of the proteins. Protein truncations, for example, specifically include the soluble portion or portions of membrane or transmembrane proteins. Protein fusions, for example, specifically include fusions of the soluble portion or portions of membrane or transmembrane proteins with soluble carrier proteins (or polypeptides).

Enzymes useful in this invention may be a truncation, variant, fusion, derivative, or semi-synthetic analog of a naturally-occurring enzyme which, for example, has been modified by modification of one or more amino acids to exhibit altered activity, e.g., enhanced activity, compared to the naturally-occurring enzyme, is a deglycosylated form of a naturally-occurring enzyme or a variant, fusion, or derivative thereof, has altered glycosylation than that of a naturally-occurring enzyme, is formed by reconstitution of an apo-enzyme with its required co-factor (e.g., FAD), is formed by reconstitution of an apo-enzyme with a derivatized co-factor. Enzyme variants, fusions, derivatives or semi-synthetic analogs of naturally-occurring enzymes may exhibit altered substrate specificity and/or altered enzyme kinetics compared to naturally-occurring forms of the enzyme.

Proteins, including enzymes, of this invention can be obtained from any source organism (e.g., microorganism, bacterium, fungus, animal, or plant). Certain sources may be preferred for use in tissue implantable sensors to avoid adverse or toxic reactions.

The term antibody (or immunoglobulin) as used herein is intended to encompass its broadest use in the art and specifically refers to any protein or protein fragments that function as an antibody and is specifically intended to include antibody fragments including, among others, Fab' fragments. Antibodies are proteins synthesized by an animal in response to a foreign substance (antigen or hapten) which exhibit specific binding affinity for the foreign substance. The term antibody includes both polyclonal and monoclonal antibodies. Polyclonal and monoclonal antibodies selective for a given antigen are readily available from commercial sources or can be routinely prepared using methods and materials that are well-known in the art. A monoclonal antibody preparation can be derived from techniques involving hybridomas and recombinant techniques. Various expression, preparation, and purification methodologies can be used as known in the art. For example, microbial expression of antibodies can be employed (e.g., see U.S. Pat. No.

5,648,237). Human, humanized, and other chimeric antibodies can be produced using methods well-known in the art.

An immunoglobulin comprises two heavy and two light chains with the former being coupled at their hinge region by disulfide linkages. The two heavy chains (but not the light chains) are different for each class of antibody, e.g. IgG, IgM, IgD, IgA and IgE. The distinctions between these classes of antibodies is understood in the art.

Fragments of an antibody can retain the binding affinity of the antibody toward antigen (or hapten). An immunoglobulin, for example IgG, comprises two heavy and two light chains with the former being coupled at their hinge region by disulfide linkages. Cleavage with papain above these linkages releases two antibody binding fragments (Fab) and a crystalline fragment (Fc). Cleavage with pepsin below the hinge results in a somewhat smaller Fc fragment and a single $F(ab')_2$ fragment with two binding sites. Each Fab fragment contains both a light chain and part of a heavy chain, and includes the sequences responsible for specific binding to an antigen. The Fc portion consists of the remainder of the two heavy chains and has effector functions, e.g. relating to binding and function of complement, macrophages and polymorphonuclear white blood cells. As noted above, the two heavy chains (but not the light chains) are different for each class of antibody, e.g. IgG, IgM, IgD, IgA and IgE.

Fabs are produced from polyclonal or monoclonal antibody preparations. Starting with polyclonal serum or hybridoma supernatant, purified immunoglobulin is digested with papain followed by purification of the Fab away from the Fc fragments generated in the digest. Commercial kits are available such as for preparation of Fab fragments from IgG (Pierce Product No. 44885; Pierce Biotechnology, Rockford, Ill.).

Alternatively, Fab' molecules are generated by using pepsin digestion of F(ab')2 fragments followed by reduction of disulfide linkage between the heavy chains, for example with cysteamine. F(ab')2 fragments are prepared and isolated by pepsin digestion using art-known techniques and materials. Fab' fragments are then obtained by reduction of the F(ab')2 followed by isolation using art-known techniques and materials. Using recombinant techniques, Fab or Fab' molecules are generated by introduction of a stop codon in the heavy chain gene at a desired location. For Fab molecules, the location can be within the hinge region at approximately the codon for the amino acid at which papain digestion occurs. For Fab' molecules, the location can approximate the pepsin cleavage point. The Fab' or Fab is then produced directly by simultaneous expression of both the light chain and engineered heavy chain genes to produced their respective proteins which assemble and are secreted from the cell.

In addition to Fab' and Fab molecules, other antibody-like molecules, and antibody-derived molecules which retain specific binding of antibodies can be employed in this invention. For example, single chain antibody variable region fragments (scFv) are employed. Furthermore, hybrid molecules such as bispecific Fab-scFv ("bibody") and trispecific Fab-(scFv)(2) ("tribody") heterodimers or multimers can be employed (Schoonjans R et al., J. Immunol. 2000 Dec. 15; 165(12):7050-7). scFv can be prepared with or without disulfide linkages. See Worn A, Pluckthun A., FEBS Lett. 1998 May 15; 427(3):357-61. scFv can be prepared from synthetic or isolated DNA, for example by starting from the actual DNA sequence of the desired scFv. An artificial gene using oligonucleotides is designed, assembled in vitro, and cloned into a suitable expression vector followed by expression in E. coli and purification of the expressed scFv. Alternatively, scFv are manufactured from monoclonal cell lines. For example, a monoclonal cell line is provided, and mRNA from the line is cloned to create a cDNA vector from which the variable heavy ($V_H$) and light ($V_L$) chains are then subcloned into an expression vector.

Other methods for production of antibody fragments are described in current editions in the series of Current Protocols titles (all generally published by John Wiley and Sons, New York), e.g. Current Protocols in Molecular Biology (edited by Frederick. M. Ausubel et al., 1991-2004, New York: Greene Pub. Associates and Wiley-Interscience: J. Wiley); Current Protocols in Immunology (edited by John E. Coligan, et al., New York: John Wiley and Sons, 1994-1998).

Sensing compositions of this invention can include carbon nanotube complexes with polysaccharides, particularly sensing polysaccharides. The term polysaccharide is used generally herein to include polymers of any monosaccharide or combination of monosaccharides. A polysaccharide typically contains 20 or more monosaccharide units. Oligosaccharide containing less than 20 monsaccharide units can be used in this invention if they are found to complex with carbon nanotubes. Of particular interest for assays for monosaccharide analytes are polymers of the monosaccharide analyte (e.g., polymers of glucose for use in assays for glucose). Polysaccharides and oligosaccharides can be derivatized with one or more chemically selective groups or moieties to impart chemical selectively to the polysaccharide.

Sensing compositions of this invention can include carbon nanotube complexes with derivatized polymers that are not proteins, polysaccharides (or oligosaccharides) or other biological polymers such as polynucleotides. Polymers which complex to carbon nanotubes and are useful in sensing compositions and methods herein include polymers which are derivatized to contain one or more chemically selective groups or moieties which impart chemical selectively to the polymer. Polymers that can be usefully derivatized include poly(ethylene glycol), polyvinyl alcohol), poly (vinyl chloride), (e.g., and copolymers thereof), and polysorbitan esters (e.g., polyoxyethylene sorbitan fatty acid esters.)

The invention relates to sensing compositions, sensing elements which are adapted to contain sensing compositions, and sensor systems. A sensing element for detecting an analyte comprises a selectively porous container adapted for receiving and retaining the components of a sensing composition. The container is sufficiently porous to allow analyte to enter the container without allowing the functional components of the analyte sensing composition to exit the container. The sensing composition is dispersed in a liquid or solid material. Typical liquids are aqueous solutions which include solutions in which the majority component is water, but which may include alcohols, glycols and related water soluble materials that do not affect the ability of the sensing composition to detect or quantitate analyte. The sensing composition may be dispersed in a solid matrix. The matrix can be formed from various polymers, silica, quartz or other glass, ceramics and metals with the proviso that the metal matrix is insulated from the surface with a coating that preserved the optical properties of the carbon nanotube/sensing polymer complexes. The matrix can be formed from a combination of such solid materials. The matrix can also be a semi-solid material such as a gel or a paste. The matrix must be sufficiently porous to allow analyte to enter without loss of sensing composition components that are needed to analyte detection. The matrix must also be sufficiently optically thin or transparent to the excitation and emission to allow detection of analytes. A solid matrix with dispersed sensing composition can serve as a sensing element. In a preferred embodiment, the sensing element is an implantable container or matrix comprising sensing composition which is biocompatible. The term "biocompatible" is employed as broadly as the term is used in the art and in preferred embodiments for human or veterinary applications the term refers to materials that cause minimal irritation and/or allergic response on implantation. The term also preferably refers to materials in which biofouling of pores is minimized.

Sensing elements include those that are implantable in tissue. Such sensors may be affected by foreign body encapsulation [31-35] and/or membrane biofouling of the sensor surface [36, 37]. Fibroblast encapsulation at the site of sensor element implantation has been reviewed [33, 34] and art-recognized solutions to this problem include administration of antigenic factors and anti-inflammatory pharmaceuticals at the site of implantation to promote neovascularization [31, 36-44]. A sensor surface may be biofouled as endothelial cells adhere and either block or in some cases consume analyte [38, 39], thus decreasing the accuracy or otherwise decreasing or destroying the function of the sensor. Sensor architecture can play a significant role in acerbating or ameliorating the biofouling problem. Biofouling necessarily limits the flux of analyte to the sensor as cellular adhesion becomes more pronounced [45]. Electrochemical sensors, which are the most widely employed for glucose detection, measure the flux of analyte (e.g., glucose) from a limiting membrane. Biofouling in such sensors immediately decreases the measured signal and is corrected only by frequent recalibration and eventually replacement is required. In contrast, optical sensors, such as those of this invention, measure the concentration of analyte at the sensor directly and fouling results in a delay in sensor response. A sensor that measures concentrations of analyte directly does not exhibit significant distortion of the measured analyte concentration until the sensor response rate becomes commensurate with the rate of change in the bulk. Implanted optical sensors will exhibit an increased stability and longer useful life on implantation compared to sensors which measure analyte flux such as electrochemical sensors.

A sensing system for detecting one or more analytes comprises one or more sensing elements (300) and a detector (310) for measuring an optical response of the complexes in the sensing solution. An exemplary sensing system is illustrated in FIG. 15. Any appropriate optical detector may be employed. The detector can include any and all necessary device elements for detecting light and converting the signal detected into a form appropriate for analysis or display. Detectors and device elements for any needed signal conversion, analysis and display are known in the art and readily available for use in this invention. It is noted that the sensing elements of the system may be remote from the detector. More specifically, the sensing system can include a source of electromagnetic radiation (305) to provide electromagnetic radiation (307) of appropriate wavelength for exciting luminescence (315) of the complexed carbon nanotube in the sensing composition which can be detected by the detector. Any known source appropriate for the sensor application can be employed including light emitting diodes, or lasers. It is noted that the excitation source may be remote from the sensor and may also be remote from the detector. In a specific embodiment, the detector and the excitation source may be combined in a single device. Those of ordinary skill in the art can select light sources and/or detectors appropriate for use in sensor systems of this invention in view of what is generally known in the art and the specific wavelengths or wavelength ranges in which the sensor is to operate.

This invention demonstrates a range of new surface assembly and chemical interactions whereby selective binding sites can be immobilized on the surfaces of individually dispersed nanotubes. These sites can then be coupled to the electronic band structure of the carbon nanotube and used to modulate the optical properties of the nanotube in response to specific molecular binding events. The term "modulate" is used broadly herein to indicate any detectible change in an optical property which can include a change in intensity of any emission, or any absorption or a change in wavelength of any absorption or emission.

In specific examples, the starting point is an ultrasonicated and purified (10) solution of HiPco nanotubes suspended according to a recently developed protocol using aqueous surfactant. The chemical species, e.g., a polymer (particularly a sensing polymer) to be complexed with the carbon nanotube is then combined with the surfactant dispersed carbon nanotubes, and dialyzed against surfactant free buffer. During dialysis as surfactant is removed complexes of the carbon nanotubes with the polymer are formed. The relative amounts of polymer and carbon nanotube are preferably selected to maximized polymer complexed carbon nanotubes and avoid excess non-complexed polymer. It may be desirable in certain cases to select the relative amounts of polymer and carbon nanotube to provide complexes which on average contain a certain number of polymer molecules complexed to a carbon nanotube. It is preferred that the relative amounts of polymer and carbon nanotube are selected to achieve monolayer or less coverage of the carbon nanotube by the polymer.

In specific embodiments, the polymer is a protein and in this case, a non-denaturing surfactant, such as sodium cholate (2% wt in buffered solution), is used in the preparation of the surfactant dispersed carbon nanotubes to prevent denaturing of the protein. The molecule to assemble is then combined with the solution, and dialyzed against surfactant free buffer (FIG. 1a.) Within certain concentration ranges van der Waals forces alone can immobilize a wide range of proteins and enzymes as a monolayer on the nanotube surface, including for example, concanavalin A, avidin, glucose oxidase, and monoclonal mouse anti-human prostate specific antigen. Above a threshold surface coverage, the process renders these systems colliodally stable, as evidenced by a preservation of fluorescence (11), and therefore individually isolated (10) even in the absence of the surfactant phase.

Figure 1B:
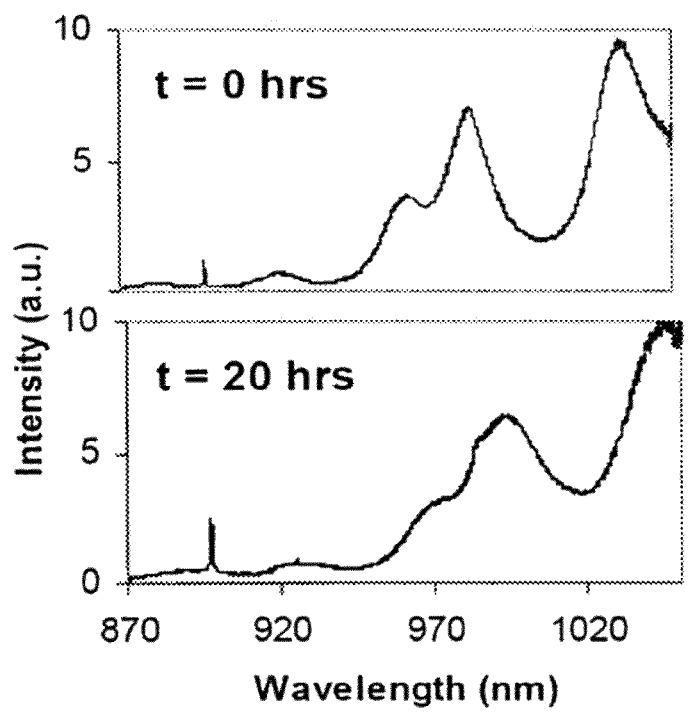
Figure 1C:
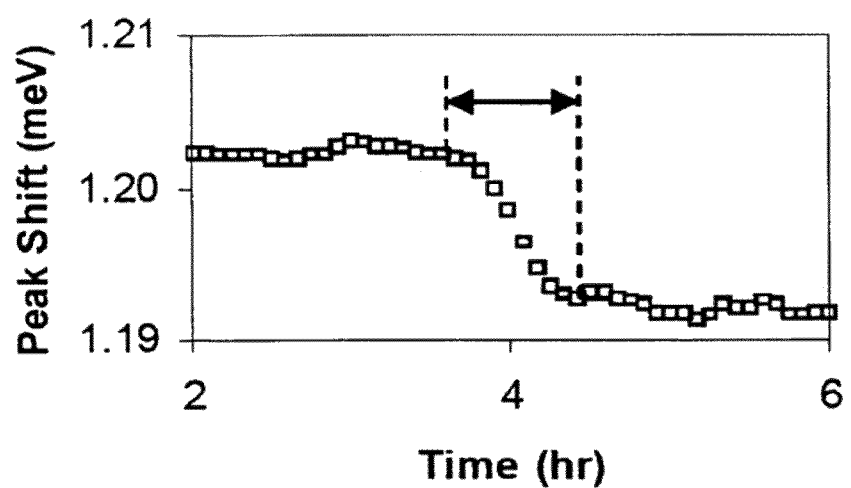

The kinetics of the assembly process can be followed using a combination of Raman and fluorescence spectroscopies as demonstrated in FIG. 1b. In the case of complexes with glucose oxidase, the system undergoes a thermodynamic phase transition after 3.8 hours upon slow removal of the surfactant as glucose oxidase is assembled along the nanotube surface. The emission maximum of the (9,1) nanotube is shown to decrease in energy by 10 meV, indicating that the tightly packed cholate adsorbed phase has been replaced by a more porous enzyme layer. The increased accessibility of water and the resulting polarity at the surface of the nanotube decreases the energy of the excited state and causes this solvatochromic shift (13).

These gaps between absorbed enzymes and proteins provide sections of exposed nanotube surface whose reactivity and electron transfer characteristics can be explored in the absence of an interfering (typically charged) surfactant layer (10, 11, 13, 16, 17) for essentially the first time. We show that non-covalent electron transfer at the nanotube surface can introduce functional groups with a preservation of electronic structure. In FIG. 2a, the exposed surface is titrated using ferricyanide ions ($Fe(CN)_6^{-3}$) which form a charge transfer complex at the nanotube thereby localizing electrons and shifting the Fermi level into the valence bands. The process can be monitored optically as the transition decays with increasing functionalization. Saturation of the exposed surface occurs at approximately 11.3 ions/unit cell length and attenuates the fluorescence from the sample by 83.3% (FIG. 2b). The surface modification is irreversible: we find that it is stable to dialysis against pure buffer indefinitely with no restoration of fluorescence or desorption back into solution. However, the absence of an increase in the nanotube disorder mode in the Raman spectrum indicates that no covalent bonds on the carbon surface have been broken (1, 2). A number of electroactive species can be immobilized in this way and used to modify the surface for desired functionality. FIG. 2b also shows the behavior of the reduction product (19) ferrocyanide ($Fe(CN)_6^{-4}$) at comparable loading. We note that the reduced electron affinity of this complex results in a less perturbing electron withdraw and only a 27.4% attenuation of fluorescence.

Figure 3:
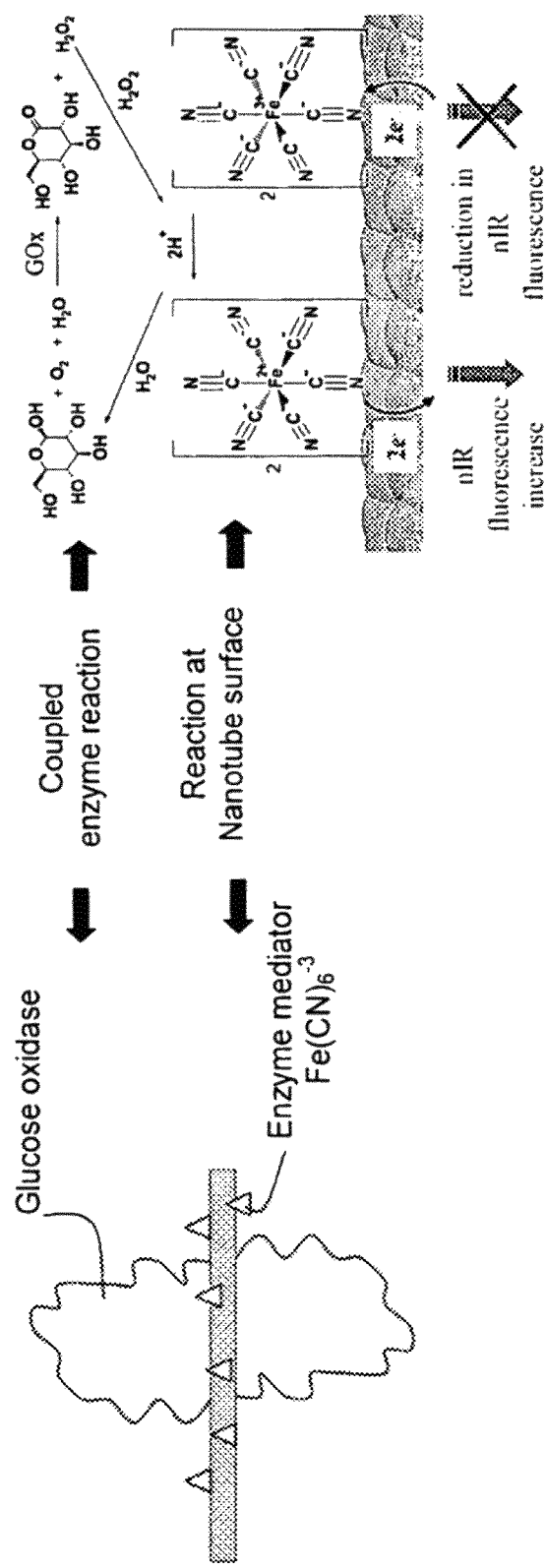
FIG. 3: Schematically illustrates coupling of an enzyme reaction (that of glucose oxidase) to the luminescence response of a semiconducting SWNT. The multi-functional tailoring on the surface of an individual carbon nanotube with enzyme and mediator couples specific binding to the optical response of the substrate. The immobilized enzyme provides sites for β-d-glucose specificity with surface functionalization of the nanotube surface with a mediator $Fe(CN)_6^{-3}$. Reaction at the enzyme coverts glucose to gluconolactone, and the hydrogen peroxide co-product is detected by interaction with the mediator at the nanotube surface. The arrangement allows for the engineering of surface functionality while retaining nanotube electronic structure and fluorescent emission.

These insights offer new routes for the chemical modification of individual nanotubes in solution in a manner that exploits, but does not disrupt, their electronic properties. For example, the electroactive ferricyanide layer can act as an enzyme mediator (19), shuttling electrons to and from β-d-glucose reaction at the enzyme layer. FIG. 3a is a molecular simulation of such a bi-functional nanotube substrate showing the coupling between the reaction at the enzyme and the electron transfer to the nanotube surface. As β-d-glucose is oxidized to the d-glucono-1,5-lactone, the $H_2O_2$ co-product reduces the mediator, which elevates the Fermi-level of the nanotube with a restoration of fluorescence. Hence, the substrate couples the binding event at the enzyme to electron transfer at the nanotube surface and modulates the fluorescence in a quantitative manner.

Figure 4A:
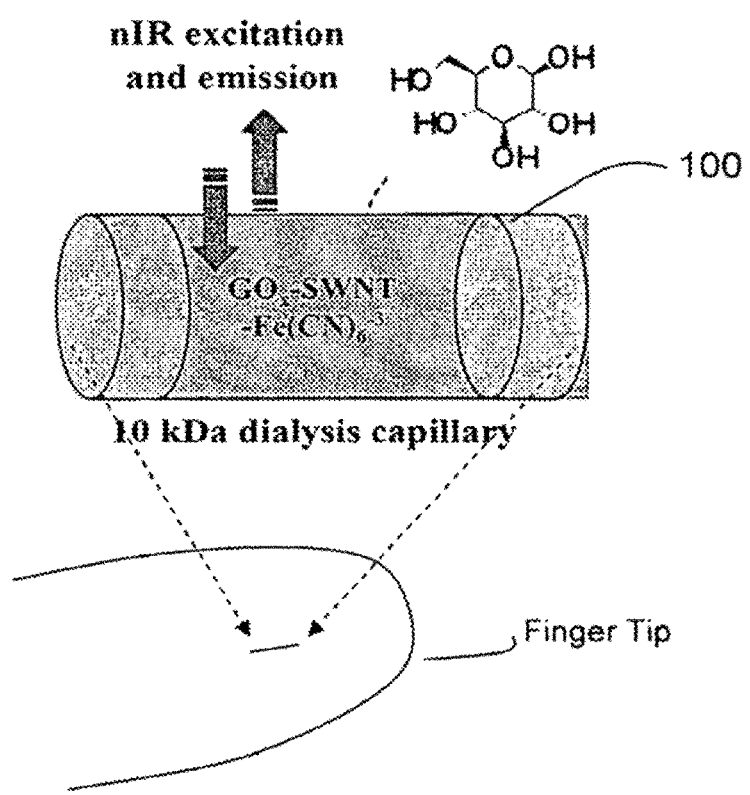
FIGS. 4A-C: Illustrates a tissue implantable device for analyte detection, exemplified for glucose detection.
Figure 4B:
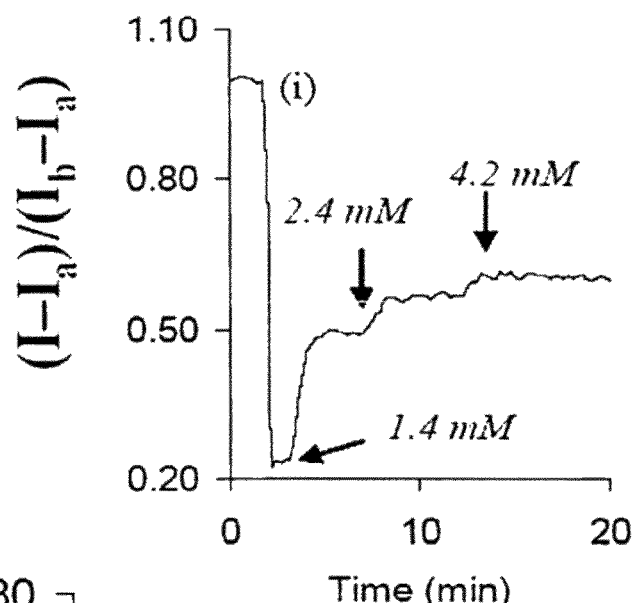

The practical utility of such a structuring of the nanotube surface is demonstrated by loading the resulting solution into a sealed 200 μm diameter dialysis capillary (13 kDa molecular weight cut-off.) Here, the target analyte is free to diffuse across the capillary boundary while the sensing medium (nanotubes with an average length of 1.5 μm) is retained. When excited with a 785 nm photodiode laser, the fluorescent emission of the (6,5) nanotube ($\lambda_{max}$=1041 nm) is shown to respond to the local glucose concentration after an 80 s transient, even in a strongly absorbing blood specimen (21). We find that adjusting the enzyme to redox mediator ratio at the nanotube surface allows for a tuning of the response into the range needed to monitor blood glucose in diabetic patients (1 to 8 mM), for instance. This tuning is done at the expense of overall sensitivity, but devices responsive in the desired range have been made with as low as 34.7 μM for the detection limit of glucose, and this corresponds to 2.2 molecules detected per nm of nanotube length. The response function (FIG. 4) relating the normalized intensity to glucose concentration follows a Langmuir adsorption profile with binding constant of 0.92 ($mM^{-1}$). The advantage of the near infrared signaling to and from such a capillary device is its potential for implantation into thick tissue or whole blood media, where the signal may penetrate up to several centimeters. Such a passive, optically responsive substrate may allow the realization of continuous analyte detection (9) in-vivo using an external, miniaturized excitation and detection device. Few organic molecules fluoresce in the wavelength range necessary for in-vivo detection, and those that do so invariably lack long term photo-stability (20). The methods described herein allow multiple functionalities to be introduced onto singly dispersed nanotubes in solution such that they retain the near infrared fluorescence. The methods herein are useful in synthesizing nanotube-based optical sensors and are further useful for preparing image contrasting agents, active biomarkers or electrodes where an isolated nanotube is desired, and the intrinsic, 1-D electronic structure must be preserved.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art prior to the invention herein, including the compounds disclosed in the references disclosed herein, are not intended to be included in the claim. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated. Specific names of compounds used herein are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, can be exchanged with "consisting essentially of" or "consisting of".

One of ordinary skill in the art will appreciate that methods, apparatus and materials, including among others, device elements, starting materials, reagents, synthetic methods, purification methods, analytical methods, and spectroscopic methods, other than those specifically exemplified can be employed in the practice of the invention without resort to undue experimentation. AU art-known functional equivalents, of any such methods, apparatus and materials are intended to be included in this invention.

Although the description herein contains many specificities, these should not be construed as limiting the scope of the invention, but as merely providing illustrations of some of the embodiments of the invention. AU references cited herein are hereby incorporated by reference in their entirety. Some references provided herein are incorporated by reference herein to provide details concerning additional starting materials and additional methods of synthesis of carbon nanotubes, additional methods of purification of carbon nanotubes, sources of proteins, for use in the invention, additional surfactants for use in the invention, additional polymers for use in the invention, more details of method for characterizing carbon nanotubes and carbon nanotube complexes, additional methods of analysis and additional uses of the invention.

The following examples are intended to further illustrate and describe the invention but are not intended to limit the invention.

The Examples

Glucose Oxidase Immobilization on SWNTs

Single walled carbon nanotubes (SWNT) product (7 mg/L) from a high-pressure CO reactor (HiPco) (Rice University research reactor run 107), were suspended in H2O with 2% wt. sodium cholate (Sigma Aldrich). The suspension was prepared using high-shear mixing, sonication and centrifugation as previously described (10) with the expectation that that 1% SDS was replaced with 2% sodium cholate. Sodium cholate is a surfactant that does not denature the protein.

Glucose Oxidase (GOx) from *Aspergillus niger* (Sigma Aldrich) was added to the cholate suspended SWNT (10 mL), to obtain a ratio of 66 mg GOx/mg SWNT in the mixture. Three milliliters of the GOx/cholate/SWNT mixture was added to a dialysis cartridge (Pierce), which was then placed into 2 liters of standard Tris buffer at pH 7.4 and dialyzed overnight. The amount of added glucose oxidase was chosen to yield a monolayer on the nanotube surface and minimize the amount of possible free GOx in the mixture that is not associated with the nanotube surface. (The preferred ratio of GOx/SWNT was empirically determined based on the phase diagram discussed below or alternatively can be estimated based on the dimensions of the protein.)

The composition of the starting solution was chosen to minimize free enzyme not adsorbed on the nanotubes. The molar ratio is (0.066 g GOx)/(160 kDa dimer GOx)(12 Da carbon)/(0.001 g nanotubes) or 1 dimer of GOx per 200 carbon atoms. For a (10, 10) nanotube, this is approximately 1 dimer on either side of the nanotube every 10 nm of nanotube length.

Figure 5:
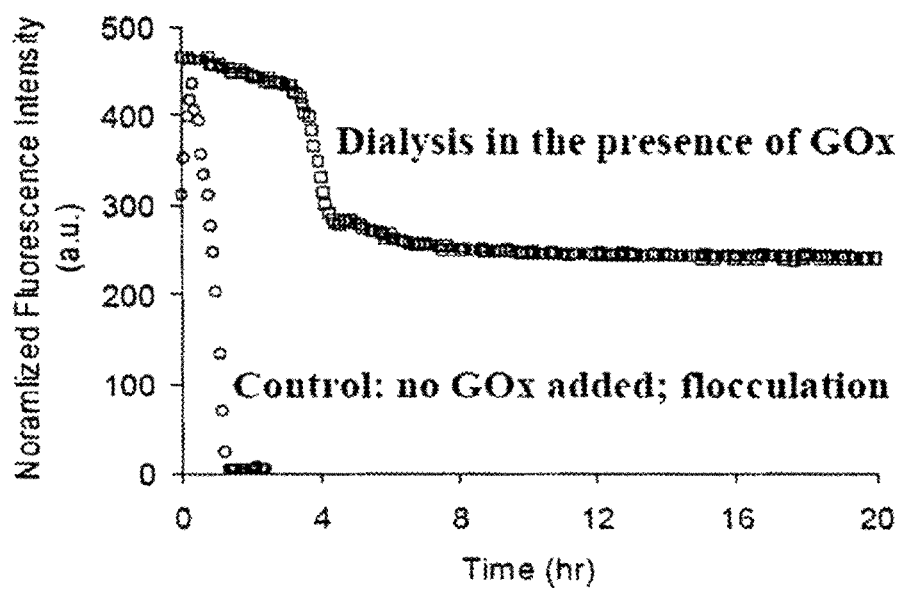
FIG. 5 is a graph showing transient fluorescence measurements of the SWNT/cholate/GOx mixture (red) and a control dialysis sample of the SWNT/cholate suspension (blue) as a function of dialysis time.

FIG. 5 is a graph showing transient fluorescence measurements of the SWNT/cholate/GOx mixture (upper line) and a control dialysis sample of the SWNT/cholate suspension (lower line) as a function of dialysis time. Fluorescence at 785 nm excitation was normalized to the Raman tangential mode at 1592 cm$^{-1}$. Fluorescence was measured using a CCD camera. As discussed above for FIG. 1B, normalized fluorescence decreases on dialysis of the SWNT/cholate/GOx mixture with a clear transition occurring at about 3.8 hrs. Ultimately fluorescence intensity is decreased by a factor of about 2.2. The control experiment was performed using identical procedures without the addition of the GOx. For the control suspension carbon nanotube fluorescence decays relatively rapidly to zero and small particles containing flocculated nanotubes are visible in the sample.

The relative stability of the SWNT/GOx suspension and the SWNT/cholate suspension after dialysis can be ascertained by visual examination. The SWNT/cholate suspension and the dialyzed SWNT/GOx suspension are translucent amber with no visible flocculation. In contrast, upon removal of the cholate by dialysis, the once dispersed nanotubes form large aggregates. If the protein is present in the dialyzed SWNT/cholate mixture above a critical concentration, the mixture is a well-dispersed suspension which is stable.

Adsorbed Phase Diagram.

Figure 6:
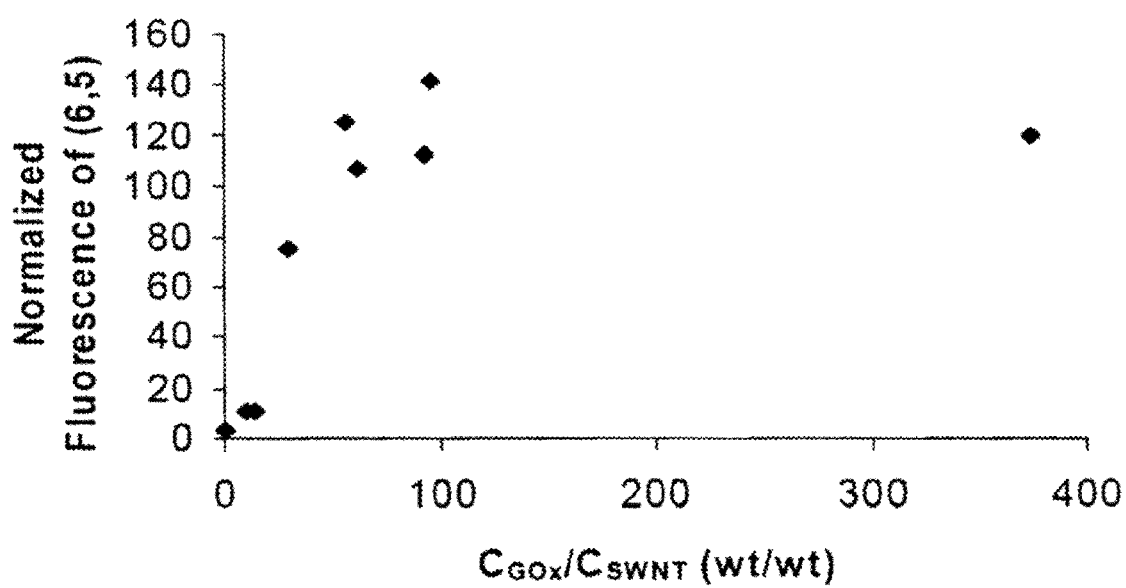
FIG. 6 is a graph of normalized fluorescence for the [6,5] carbon nanotube as a function of the weight ratio of GOx (protein) to SWNT in SNWT/cholate/GOx samples after (20 hrs) dialysis.

FIG. 6 is a graph of normalized fluorescence as a function of the weight ratio of GOx (protein) to SWNT in SNWT/cholate/GOx samples after dialysis (approximately 20 h). Lowering the starting concentration below the threshold used for the above experiments results in a flocculated system. Using nanotube fluorescence and its absence upon aggregation, a phase diagram can be made for the system being studied. Here, the measured fluorescence is normalized by the intensity of the tangential Raman mode measured at 785 nm.

Based on these data it was determined that a GOx to SWNT ratio of about 66:1 or higher is preferred to solubilize all of the nanotubes in the sample and to minimize the amount of free enzyme in solution.

Figure 7:
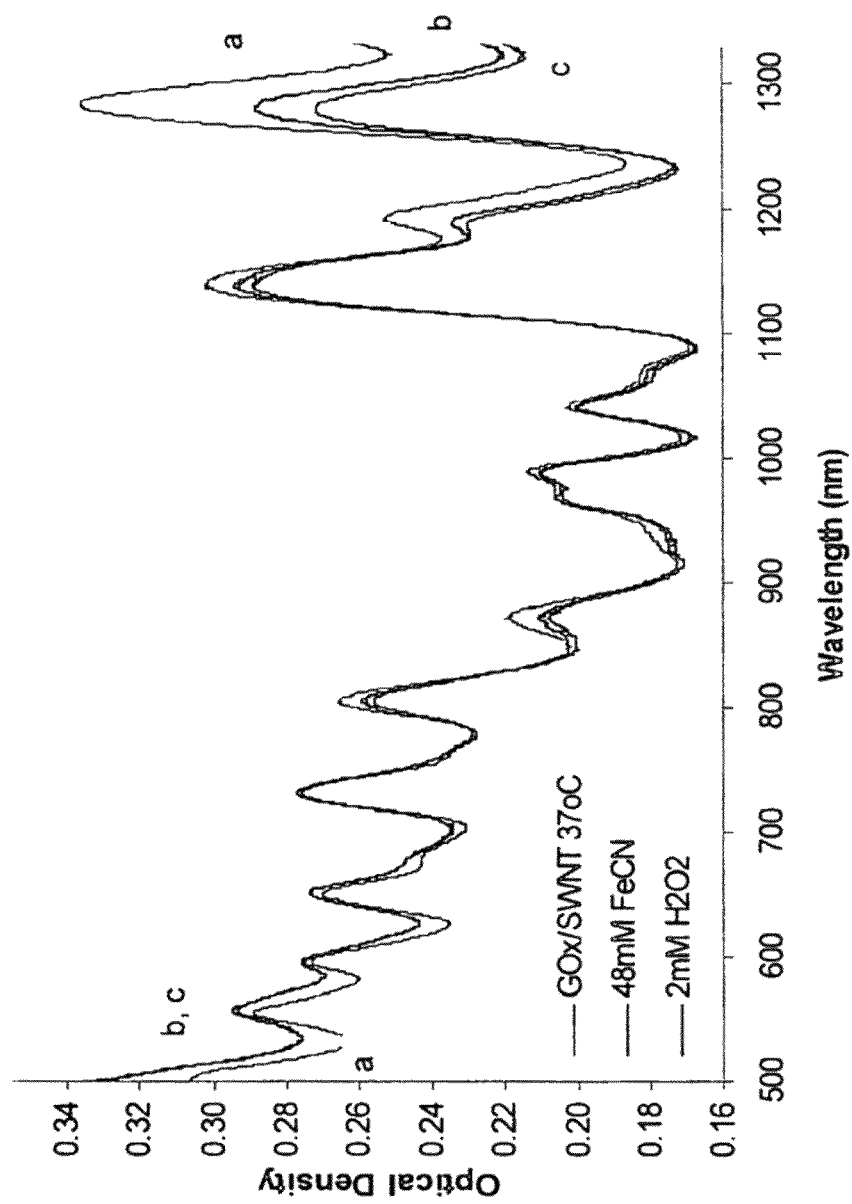
FIG. 7: Ultraviolet visible near infrared absorption spectrum of GOx/SWNT complex maintained at 37° C. (spectrum a). After addition of 48 mM ferricyanide (spectrum b) E11 transitions above 1100 nm decrease while transitions between 900 and 1100 nm remain unchanged. The apparent increase in absorption between 500 and 700 nm is due to ferricyanide absorption in the visible. The solution was then titrated with 2 mM hydrogen peroxide (spectrum c) resulting in only a partial restoration of the longest wavelength excitations and no change in the other spectral features.

The UV/near infrared absorption spectrum of the GOx/SWNT complex (at 37 C) is shown in FIG. 7 (spectrum a). After addition of 48 mM ferricyanide (spectrum c) E11 transitions above 1100 nm decrease, while transitions between 900 and 1100 nm remain unchanged. The apparent increase in absorption between 500 and 700 nm is due to ferricyanide absorption in the visible. The solution was then titrated with 2 mM hydrogen peroxide (spectrum b) resulting in only partial restoration of the longest wavelength excitations and no change in the other spectral features.

SWNT/GOx Sensor Testing.

A reactor setup was used to test the SWNT/GOx glucose sensor. The sensing medium, GOx-SWNT or the control 2% wt, cholate-SWNT, was loaded into a dialysis cartridge (having a 10 KDa molecular weight cutoff) and placed in TRIS (pH 7.4) buffer in a reaction chamber. A temperature controller with a heating coil and a thermocouple was used to maintain temperature at 37° C. A peristaltic pump was used to cycle reagent-free buffer into and remove buffer from the reaction chamber. The fluorescent emission of nanotubes was detected using a long-distance objective lens via a thermoelectrically-cooled CCD (Andor) with 785 nm excitation from a photodiode laser.

Figure 8:
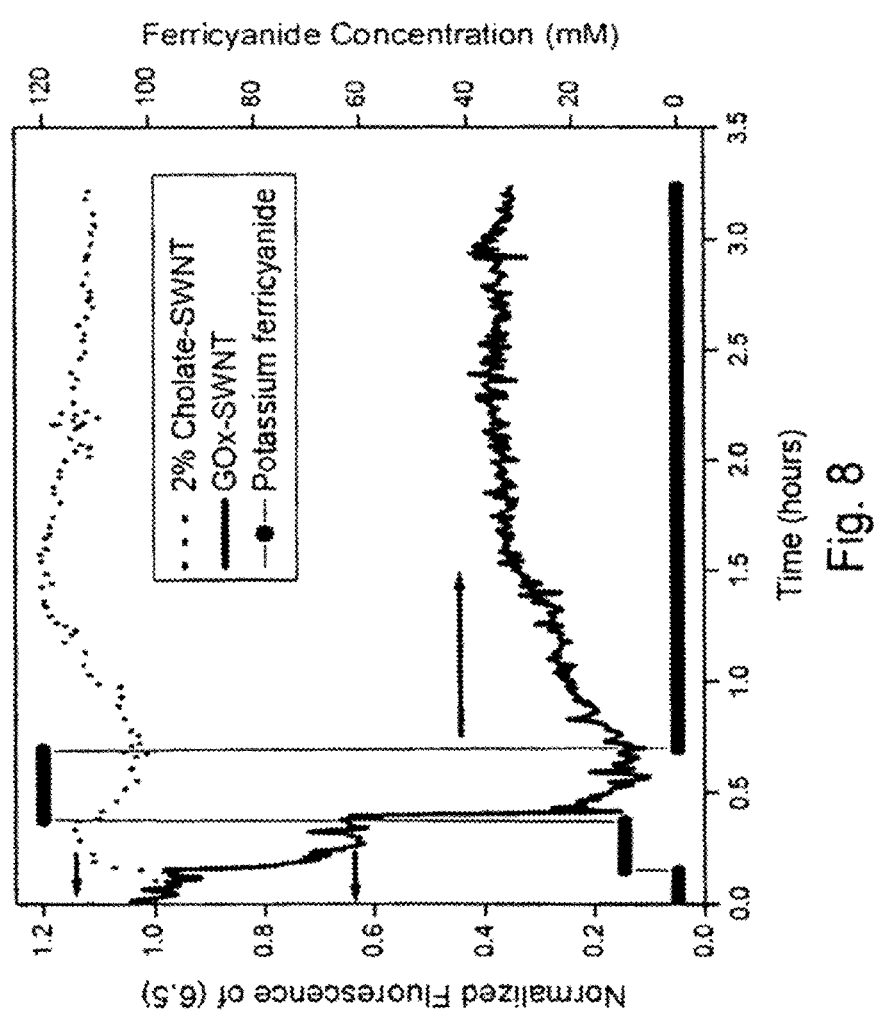
FIG. 8 is a graph showing the effect of additions of ferricyanide to a sensing medium containing GOX-SWNT complexes.

Aliquots of 0.5 M potassium ferricyanide solution were added directly to the stirred buffer in the reaction chamber to adjust the concentration of ferricyanide therein. Potassium ferricyanide, is free to diffuse across the membrane, while the sensing medium (SWNT/GOx) containing nanotubes is retained in the cartridge. FIG. 8 is a graph showing the effect of additions of ferricyanide to the sensing medium by dialysis into the dialysis cartridge. The fluorescence of GOx-SWNT diminishes in response to ferricyanide addition. Cycling in reagent free buffer (dropping ferricyanide concentration in reaction chamber to zero) results in only a partial restoration of fluorescence intensity. It is believed, as discussed above, that a portion of the ferricyanide is chemisorbed to SWNT/GOx complexes and is not removed. The same experiment was performed with a control of 2% wt. cholate suspended SWNTs. No diminution in fluorescence was observed on addition of ferricyanide.

Glucose Sensing.

Figure 4C:
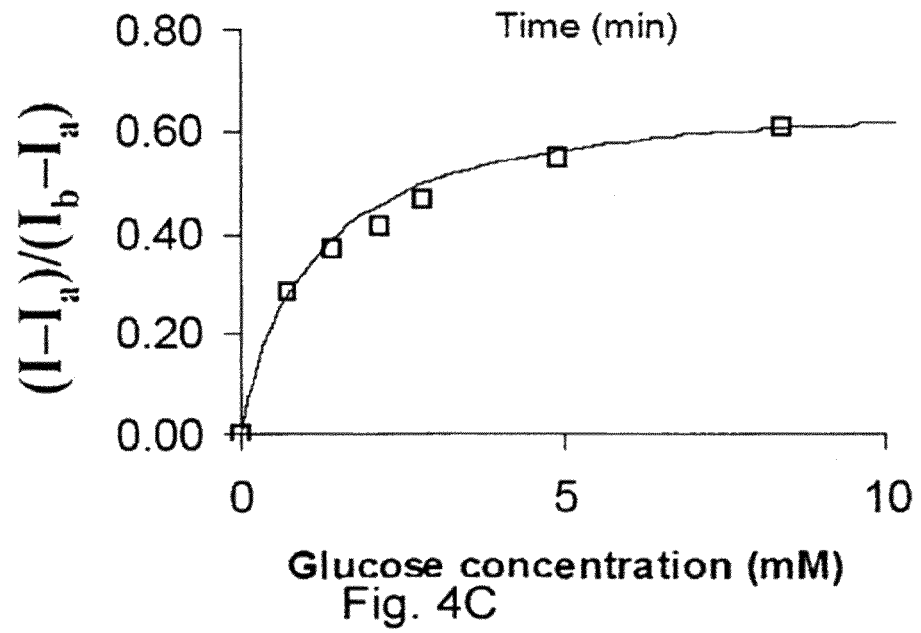

A SWNT/GOx suspension prepared as described above having a 66:1 weight ratio of GOx:SWNT (600 microL) was introduced into a cuvette maintained at 37 C. The sample was excited using a 785 nm laser (power 35 mW) and the resultant near-infrared (nIR) fluorescent light was scattered back 180° and recorded using a nIR sensitive CCD camera. While continuously monitoring the nanotube fluorescence, 100 microL of the potassium ferricyanide solution (0.5 M) was added to the cuvette (62.5 mM) leading to a fluorescence decrease. Once the fluorescence reached a steady state value, 4 microL of glucose (1.2 mM) in 0.5 M phosphate buffer (pH 7.4) was added, giving a total initial glucose concentration of 1.42 mM in the cuvette. This process was repeated twice more, each time adding a 4 microL injection of glucose to increase the glucose concentration in the cuvette to 4.2 mM and 7.0 mM, respectively. As shown in FIG. 4C normalized fluorescence intensity increased with addition of increasing concentration of glucose.

Glucose Sensing Control Experiments.

Figure 9A:
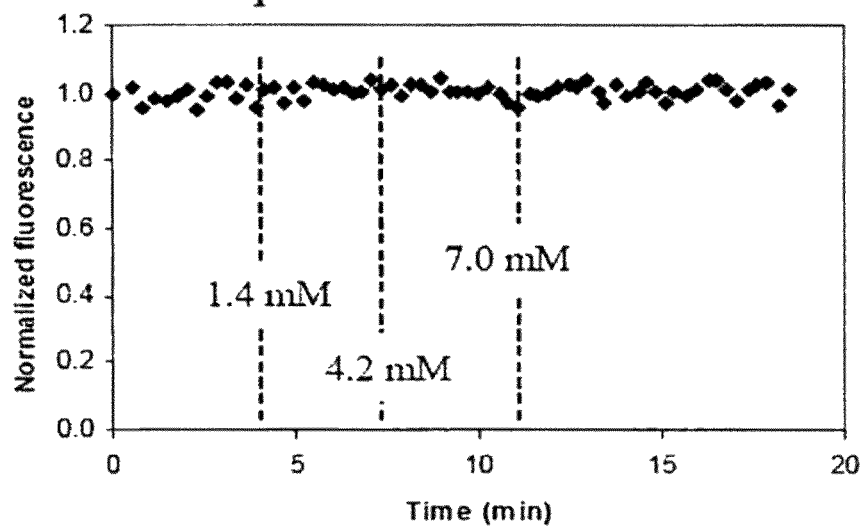
FIGS. 9A and 9B are graphs showing fluorescence response in control glucose sensing experiments.
Figure 9B:
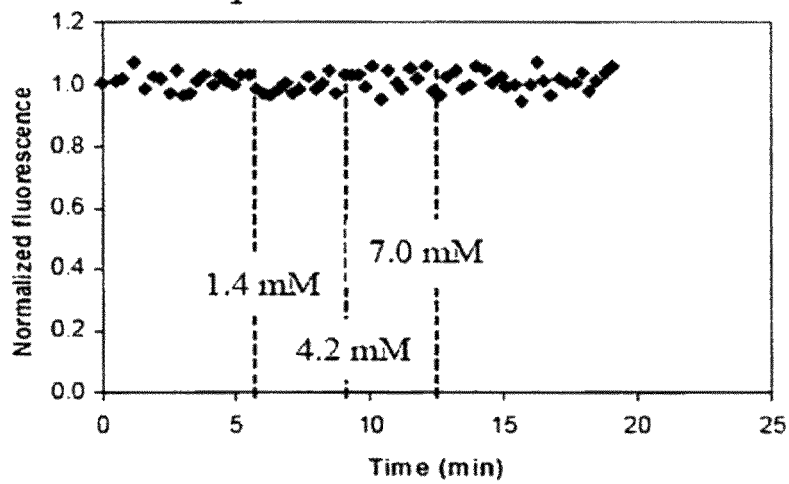

Control glucose sensing experiments were performed using 2% cholate suspended SWNT and GOx-SWNT without addition of ferricyanide. These suspensions were both buffered (pH 7.4) and maintained at 37 C. As shown in FIGS. 9A and 9B, no significant change in fluorescence was observed on glucose addition in these control experiments.

Glucose Sensing in Pig Serum.

GOx suspended SWNT (GOx:SWNT weight ratio=66:1) was injected into a dialysis capillary (Spectrum) with a 13 kDa MW cutoff and the dialysis capillary was inserted into a small diameter, ~1-2 mm, glass capillary. The dialysis capillary was closed using a cyanoacrylate adhesive. One end of the glass capillary containing the dialysis capillary was inserted into 0.5 M phosphate buffer (pH 7.4) at 37 C, causing the buffer to fill the glass capillary. Laser light of 785 nm (35 mW) was focused onto the capillary with the fluorescence emission being scattered back 180° through a notch filter illuminating a CCD camera used to record the signal. Approximately 1 mL of a 62.5 mM potassium ferricyanide solution in phosphate buffer (pH 7.4, warmed to 37 C) was then injected into the glass capillary displacing the buffer therein and causing ferricyanide to diffuse into the dialysis capillary with a resultant decrease in nanotube fluorescence. The solution in the glass capillary surrounding the dialysis capillary can be replaced with ferricyanide-free buffer with no restoration of the fluorescence as discussed above. Pig serum from a pregnant female warmed to 37 C, was then injected into the glass capillary allowing serum glucose to diffuse through the membrane and register a response.

Determination of GOx Kinetic Constants.

Figure 10:
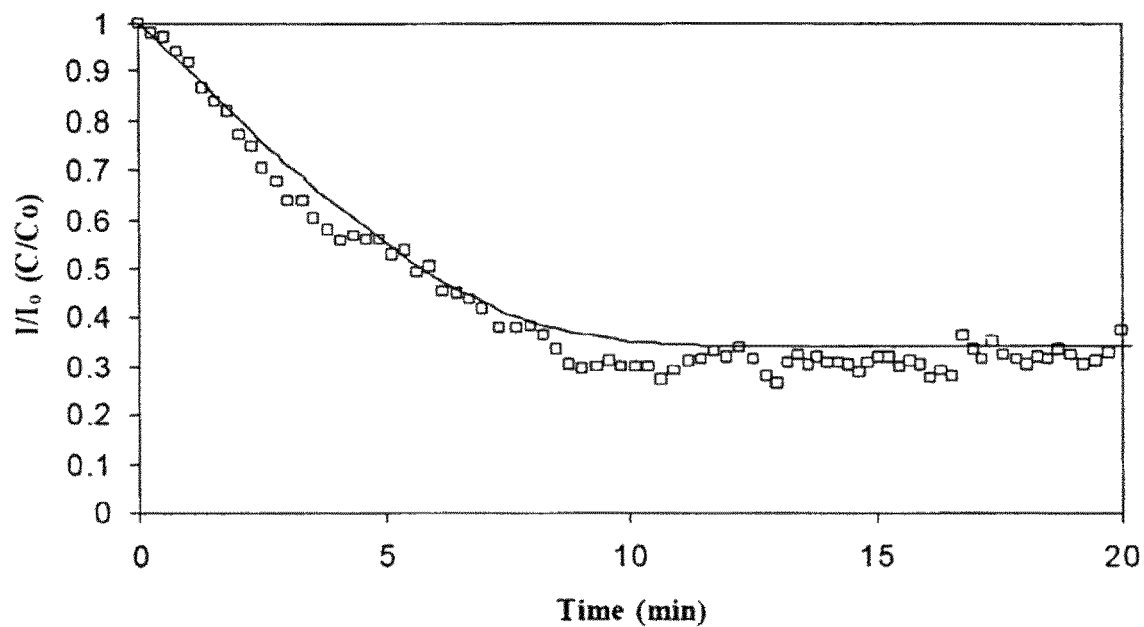
FIG. 10 shows normalized response of $Fe(CN)_6^{3-}$ scattering intensity (□) monitored via Raman scattering at 785 nm at 2132 cm$^{-1}$ after addition of 20 mM glucose. The glucose was added to a solution of 0.0127 mM GOx and 62.5 mM $Fe(CN)_6^{3-}$ in 0.5 M phosphate buffer at pH 7.4 and 37° C. The solid line is the fit of the calculated normalized ferricyanide concentration.

To determine GOx kinetic constants under the sensing conditions, 600 microL of GOx (0.0127 mM) in 0.5 M phosphate buffer (pH 7.4) and 100 microL of the 0.5 M ferricyanide solution (in 0.5 M phosphate buffer, pH 7.4) were well mixed and maintained at 37 C in a jacketed cuvette. The sample was illuminated with a 785 nm laser and the resultant ferricyanide Raman scattering from the mediator, evident at 2132 $cm^{-1}$, was collected at 180° and recorded by a CCD camera. While continuously monitoring the ferricyanide Raman scattering peak, 100 microL of glucose solution (20 mM) was added to the cuvette. The oxidation of glucose by glucose oxidase caused hydrogen peroxide to be produced, which then reduced the free ferricyanide, $Fe(CN)_6^{3-}$, to ferrocyanide, $Fe(CN)_6^{4-}$, resulting in an intensity loss from ferricyanide scattering. Ferricyanide scattering intensity was normalized to one by dividing the specific intensity by the initial intensity. FIG. 10 shows the change in normalized ferricyanide scattering intensity monitored via Raman scattering at 785 nm at 2132 $cm^{-1}$ over time after addition of 20 mM glucose. The same experiment was also completed for glucose concentrations of 31, 10 and 5 mM. The ferricyanide response was fit with a normalized ferricyanide concentration, $C/C_o$, modeled using Michaelis-Menton kinetics $$\frac{I}{I_0} = \frac{C}{C_0} \approx -\frac{d[G]}{dt} = \frac{k_2[GOx][G]}{K_m + [G]}$$

where $I_0$ and $I$ are the initial and transient ferricyanide scattering intensity, [G] is the glucose concentration, [GOx] is the total enzyme concentration, $K_m$ is the Michaelis-Menton constant and $k_2$ is the reaction rate constant. Fitting all four data sets yields kinetic constants $K_m$=421 mM and $k_2$=293.4 $min^{-1}$. The fit of the model for one response can also be seen in FIG. 10.

Determination of GOx Activity in the GOx/SWNT Complex.

Figure 11:
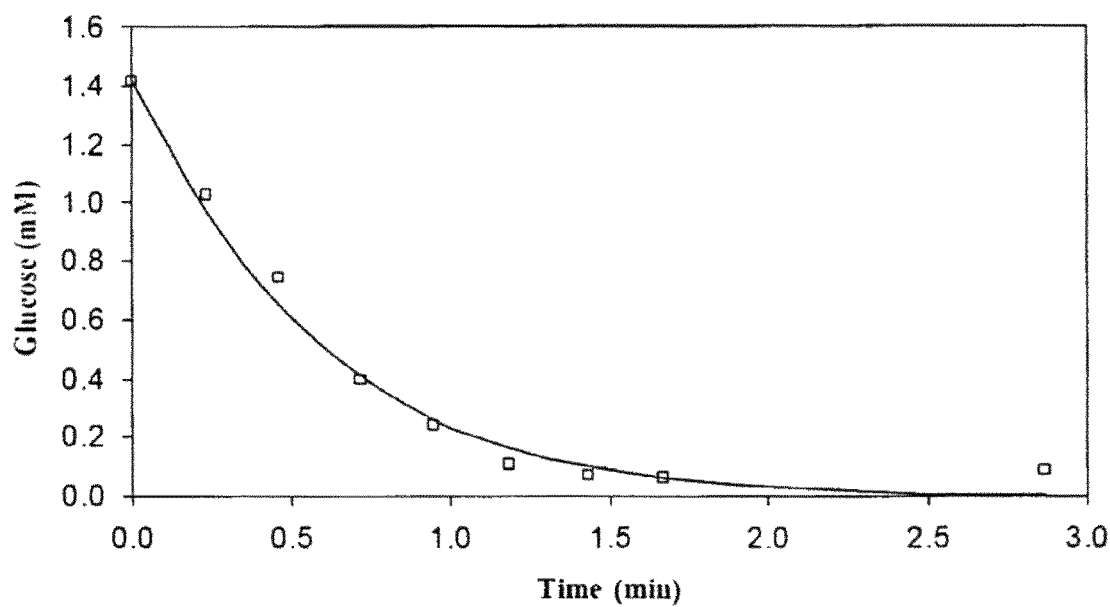
FIG. 11 shows the change in glucose concentration after first glucose injection in sensing buffer calculated from fluorescent data (□) and the corresponding model using an effectiveness parameter of 5.61 and kinetic parameters $K_m$=4.21 mM and $k_2$=293.4 min$^{-1}$.

Nanotube fluorescent data from sensing glucose in buffer was used to determine the effective GOx concentration under identical conditions as above. Fluorescence intensity was normalized to $(I-I_b)/(I_a-I_b)$ where $I$ was fluorescence intensity, $I_a$ was fluorescence intensity of pristine nanotubes and $I_b$ was fluorescence intensity after the ferricyanide adsorbed to the nanotube surface. The normalized intensity was then used in conjunction with the glucose response function to calculate glucose concentration for each data point. Using the previously calculated $K_m$ and $k_2$, the effectiveness factor, defined as the effective GOx concentration divided by the actual GOx concentration, was calculated. The change in glucose concentration was again described using Michaelis-Menton kinetics, and the GOx concentration was modified to give the best fit to the data. This modified GOx concentration was then considered the effective GOx at the SWNT sidewall. The method of least squares was used to minimize error between the calculated and experimental glucose concentrations. The fit of the first glucose injection during sensing in buffer can be seen in FIG. 11 (the line represents the model and the squares are the data.).

A comparison of these responses reveals no loss of GOx enzyme activity while attached to the carbon nanotube surface. Hence, the enzyme is not denatured or inactivated, but quite stable despite the dialysis process.

AFM Analysis of GOx-SWNT and Controls.

Tapping mode atomic force microscopy (AFM) of glucose oxidase and glucose oxidase-suspended nanotubes (GOx-SWNT) was performed with a Digital Instruments Multimode IIIa Scanning Probe Microscope (Veeco Instruments, Woodbury, N.Y.) using 100 um v-shaped cantilevers with oxide-sharpened silicon nitride tips (Veeco Metrology LLC., Santa Barbara, Calif.) Samples were suspended 10 mM Tris buffer at a pH of 8 with 0.15 M NaCl and 10 mM $MgCl_2$ and deposited onto a mica surface. Wet AFM images were made in buffer. Review of these images indicates an average height of 4.4 nm suggesting monolayer coverage of glucose oxidase on the carbon nanotubes.

Control AFM images of HiPco nanotubes were taken in tapping mode with a Digital instruments 3100 Scanning Probe Microscope using BS-Tap300Al aluminum-coated silicon tips (Budget Sensors, Sofia, Bulgaria). Nanotubes suspended in 100 mM sodium cholate were deposited onto a silicon wafer coated with 3-aminopropyltriethoxy-silane and rinsed after 20 seconds. Images were taken on the dried surface. Height measurements of these carbon nanotubes are typically between 0.6 and 1.5 nm.

Delectability of SWNT Near-IR Fluorescence through a Tissue Sample.

A capillary loaded with GOx suspended SWNT was placed underneath a sample of cultured human epidermal keratinocytes (MatTek). An area map measured at 20× magnification monitoring nanotube fluorescence at 785 nm excitation clearly shows an image of the capillary through the tissue sample. Fluorescence of a semiconducting carbon nanotube is readily detectable though the tissue sample.

Estradiol-17β(E2) Sensor.

Figure 12:
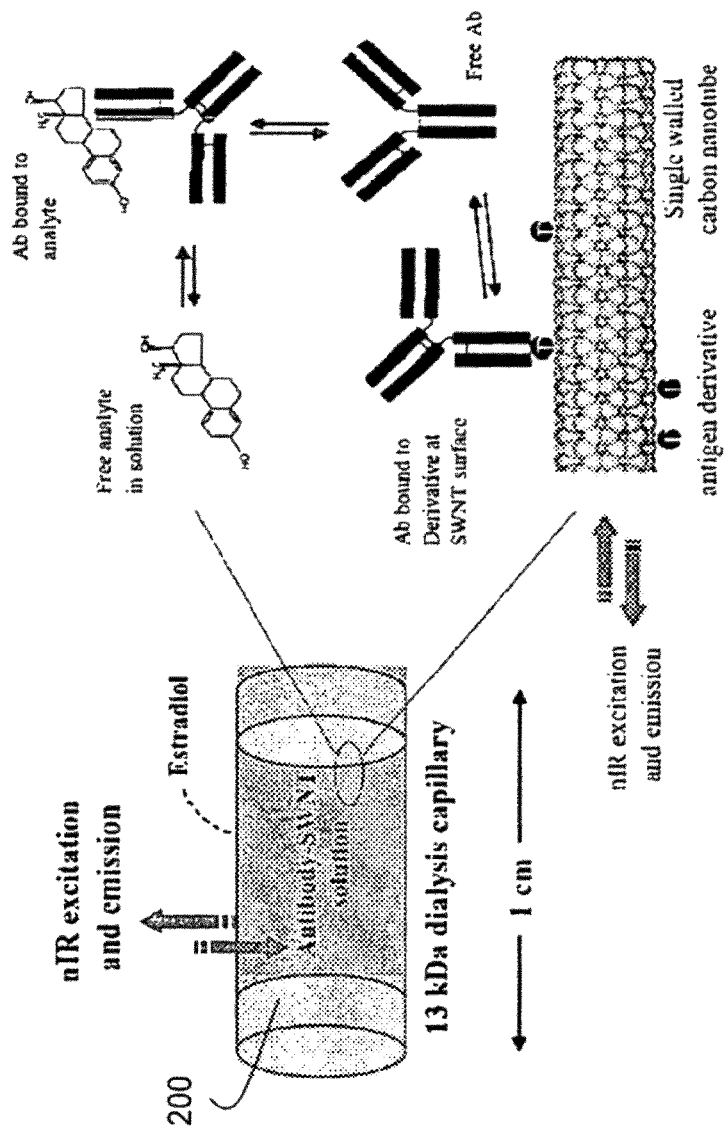
FIG. 12 is a schematic of an exemplary sensor comprising a sensor element which is a dialysis capillary (200) based on competitive binding of an antibody to an analyte derivative (bound to a sensing polymer in the SWNT/sensing polymer complex) and a free analyte. The sensor is exemplified for detection of estradiol-17β (E2).
Figure 13:
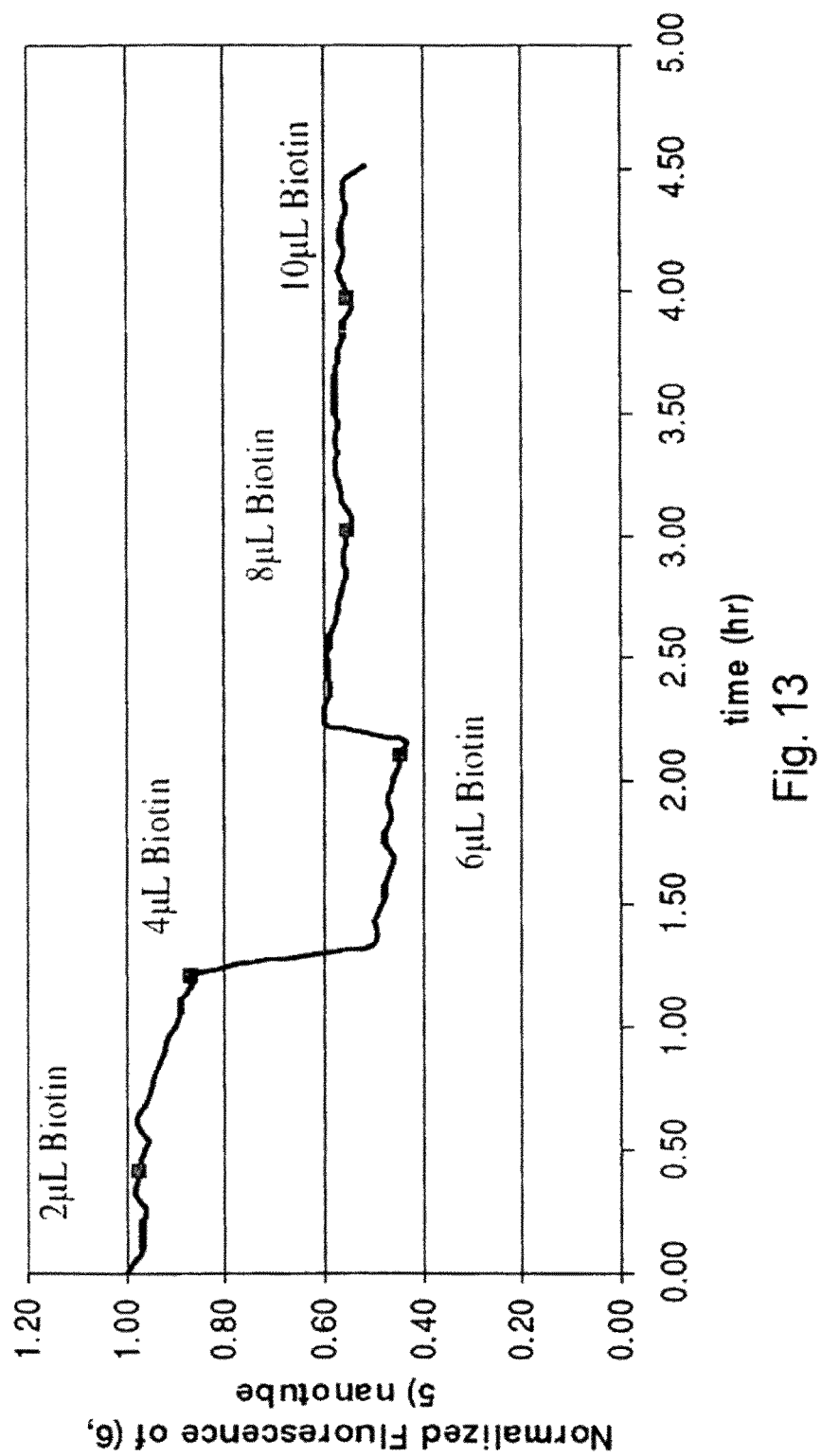
FIG. 13 is a graph showing the change in fluorescence change of Avidin suspended SWNT with additions of Biotin, see the Examples.

FIG. 12 illustrates an estradiol-17β(E2) sensor in which a sensing polymer covalently derivatized with one or more E2 molecules (antigens) or E2 derivatives (antigen derivatives) is non-covalently complexed with carbon nanotubes, specifically with semiconducting carbon nanotubes which exhibit band gap fluorescence. A sensing solution comprises carbon nanotube/sensing polymer complexes and antibody that specifically binds to the antigen and the covalently linked antigen or antigen derivative. The analyte detected is the antigen. As free (unbound) antigen comes into contact with the analyte sensing composition, it binds to free antibody (in equilibrium with bound antibody) and shifts the equilibrium of antibody bonded to the covalently attached and free antibody toward free antibody which is detected by as an increase in near IR fluorescence of the carbon nanotube. The sensing polymer may be a polymer derivatized with one or more antigens or antigen derivatives (the antibody must have some affinity for binding to the antigen derivative.) The concentration of the antigen in contact with the sensing solution is determined by following changes in fluorescence (intensity or wavelengths shift.) For example, poly(ethylene glycol) can be functionalized with a derivative of 17β-estradiol, 3-(O-butyric acid)estradiol using a procedure similar to that described in the BIAcore system Manual, BIAcore Uppsala Sweden 1991 for treatment of Surface Plasmon Resonance surfaces. Alternative derivatization methods are known in the art.

As an alternative, the sensing polymer can be a protein scaffold with estradiol or estradiol derivatives covalently attached thereto.

As illustrated in FIG. 12, an analyte sensing solution containing the carbon nanotube complex with the sensing protein and containing antibody is introduced into a dialysis capillary to form a sensor element. As shown, the sensor element may be implanted in tissue or contacted with a biological fluid to assess levels of E2 in the tissue or biological fluid. The sensing composition components illustrated in FIG. 12 can be employed to detect antigens including steroids, other than estradiol.

The illustrated E2 sensor can be employed, for example, for tracking estrus in an animal, particularly in cows and pigs. Measurement of E2 levels will allows improved timing of insemination of animals and can be used to monitor pregnancy in the animals. Sensors for the detection of the presence of and concentration of other steroids in tissue or biological fluids can be made in an analogous manner.

Preparation of Avidin/Carbon Nanotube Complexes.

Avidin suspended SWNT were prepared using dialysis as described above. SWNT decant suspended in 2% cholate and 1× Tris buffer were combined with avidin in a 3 mL dialysis cassette. The cassette system was dialyzed once for 17 hours in 500 mL of lightly stirred 1× Tris buffer, then dialyzed again for 14 hours in 2 L of the buffer. Spectra of the initial and final solutions were taken using fluorescence and Raman scattering to confirm that the SWNT did not bundle during the dialysis process. Avidin suspended SWNT containing individually dispersed carbon nanotubes which exhibited band gap fluorescence. A commercial avidin preparation was employed. Streptavidin or avidin from egg white can be employed. Additionally various labeled avidins can be employed.

Biotin interaction with the avidin suspended SWNTs was probed using fluorescence and Raman scattering. The avidin SWNT suspension was pipetted into a quartz cuvette, and stirred while continuous spectra were taken every 3.3 min, monitoring the area under the fluorescence peak for the (6,5) nanotube (see FIG. 14.) After 30 minutes, 2 µL of biotin in water (0.22 µg/µL) were added to the avidin SWNT system, inducing a gradual decline in the fluorescence peak area. Four additional aliquots of 2 µL biotin were added in 1 hour intervals. The second addition of biotin produced a 50% drop in the peak area within 6.5 minutes. However, the following biotin addition caused a 25% recovery of the fluorescence within 3.3 minutes, then a slow steady decrease. Subsequent biotin additions resulted in an immediate increase in fluorescence, followed by a slow decline of the peak area. These results demonstrate that fluorescence emission of avidin suspended SWNTs are sensitive to binding of biotin and can be employed for sensing applications on the nanomolar level. Avidin suspended SWNTs which contain avidin complexed with single-walled carbon nanotubes exhibit near IR fluorescence and are particularly useful in implantable sensors. Avidin suspended SWNTs can be used to detect biotin and various biotin derivatives as well as biotinylated species. Avidin suspended SWNTs can be used to detect various chemical and biological species that have been subjected to biotinylation. Biotinylation kits are available from commercial sources for a variety of applications.

An Optical Glucose Sensor Based on Competitive Binding.

Figure 14A:
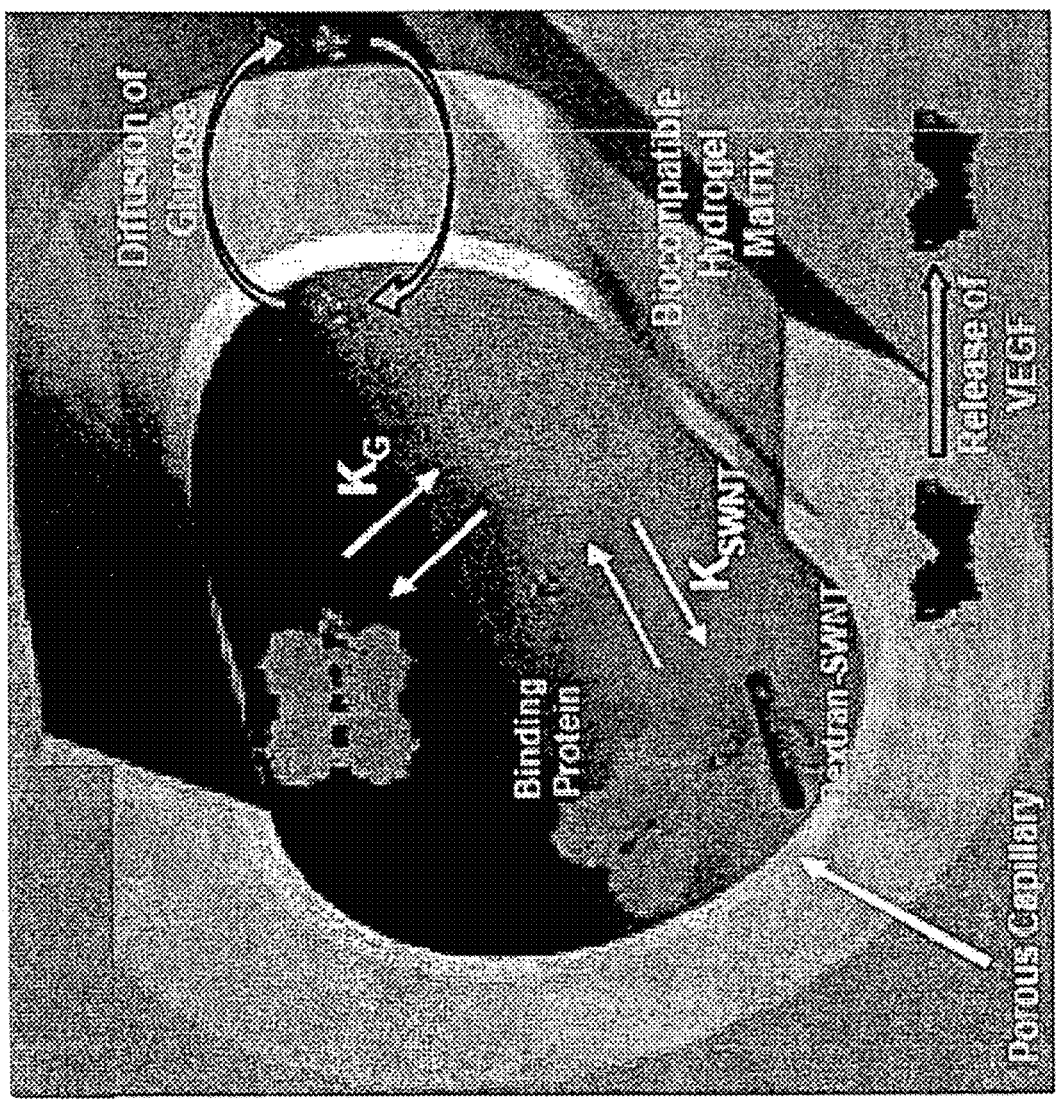
FIG. 14 A is a schematic illustration of a carbon nanotube optical sensor for glucose detection that can be implanted beneath the skin where the sensing medium is contained in a dialysis capillary encased in a biocompatible hydrogel matrix.

A reversible glucose sensor using SWNTs as the fluorophore that is based on competitive binding is illustrated in FIGS. 14A and B. FIG. 14 A illustrates a sensing element particularly for implantation into tissue. FIG. 14 B illustrates the mechanism of the competitive binding that is the basis of the sensor. Nanotubes are complexed or coated in a polymer that functions as a glucose analog, such as dextran, for binding to or reaction with a glucose-specific protein. Specifically, the sensing composition comprises SWNT/dextran complexes, and a known concentration of the a protein that binds selectively to glucose (and the dextran polymer). Specific examples of such proteins include apo-glucose oxidase, which retains glucose binding function, but not its enzyme activity, or the glucose-binding lectin, concanavalin A (ConA). The sensor element of FIG. 14A is shown for implantation and employs a biocompatible hydrogel which optionally comprises growth factors such as VEGF for release into the surrounding tissue.

Figure 14B:
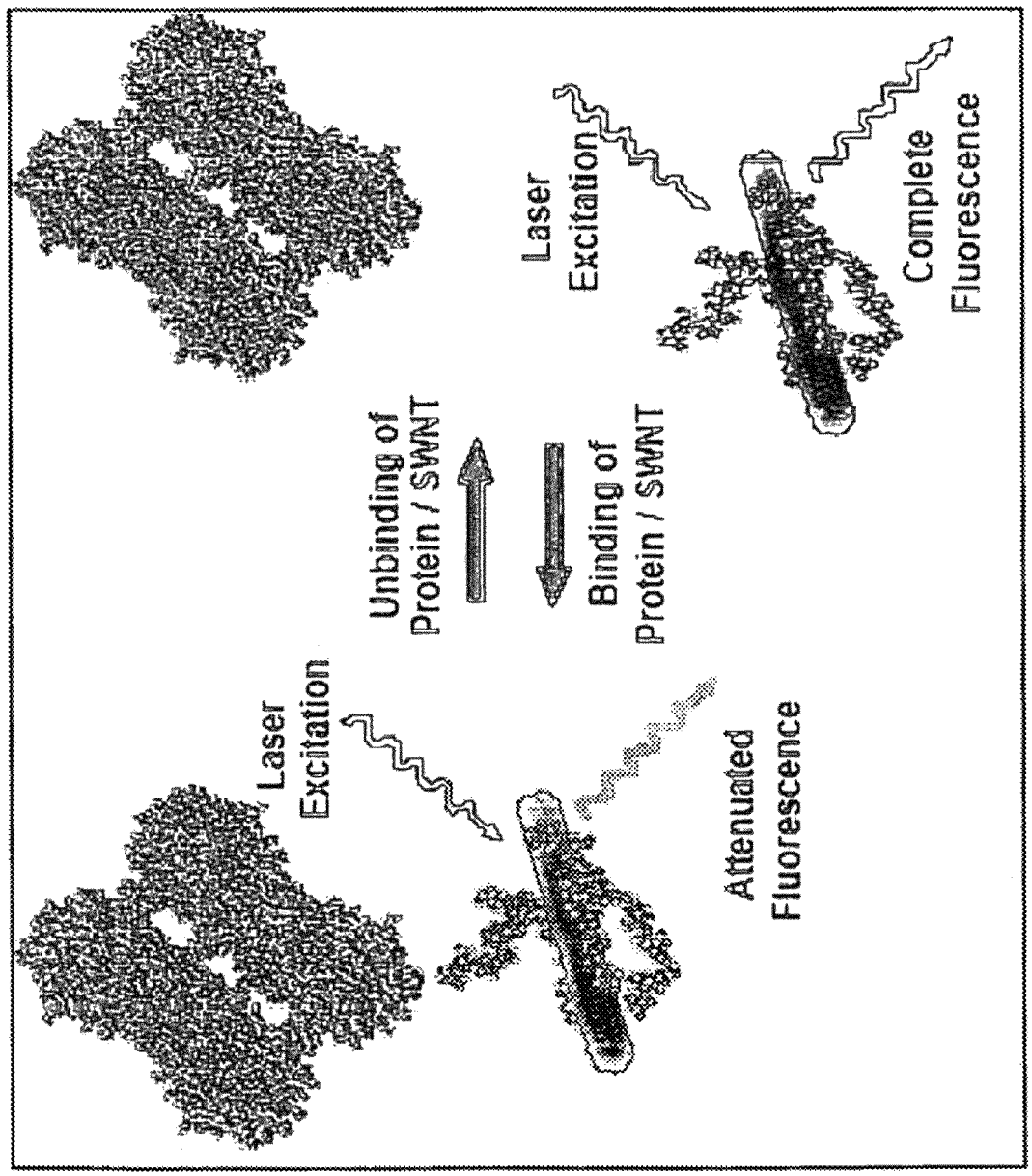

Binding of protein to the polymer (dextran) at the surface of the nanotube attenuates SWNT fluorescence, which is reversed by the introduction of glucose into the system (FIG. 14B). The sensing composition containing the SWNT/dextran complex and the glucose selective protein is then introduced into a dialysis capillary with a molecular weight cutoff such that the sensing composition is retained and glucose can freely diffuse across the barrier.

The capillary is preferably coated with a porous, biocompatible hydrogel, such as described in [48-51] to reduce or prevent encapsulation and detriment to the sensing device. Growth factors, such as vascular endothelial growth factor (VEGF), can be imbedded in the hydrogel matrix and released in a controlled manner to induce vascularization [48] around the capillary. Once implanted beneath the skin excitation of the sample can be accomplished using a laser diode coupled with an InGaAs detector array, as illustrated in FIG. 15. The sensor system illustrated in FIG. 15 can be employed for a variety of sensing compositions of this invention.

To understand the sensor response, the equilibrium response of the sensor can be modeled. The total amount of binding protein bound to the surface of the nanotube can be determined using the equilibrium binding constants for the two competitive reactions, $$K_G = [\text{Protein-Glucose}]/[\text{Protein}][\text{Glucose}]$$

$$K_{SWNT}[\text{Protein-SWNT}]/[\text{Protein}][\text{SWNT}]$$

where KG is the equilibrium binding constant for binding protein and glucose, KSWNT is the equilibrium binding constant for binding protein and dextran coated SWNT, [Protein-Glucose] and [Protein-SWNT] are the concentrations of binding protein bound to glucose and SWNT, respectively, and [Protein] and [Glucose] are the concentrations of each unbound species. Finally, [SWNT] is the total concentration of unbound protein binding sites on the surface of the nanotube. To estimate the total number of binding sites on the surface of the nanotube, reasonable assumptions are that the nanotube concentration is 50 mg/L, each nanotube is ~1 µm long, and that there is a protein binding site every 10 nm along the SWNT surface, giving a binding site concentration of ~10 µM. Because proteins localized near the surface of the nanotube attenuate SWNT fluorescence, the normalized fluorescence from the sensor can be modeled as (Total Surface Occupied Surface)/Total surface. Finally, using equilibrium constants for ConA as an estimated (KG=400 L/mol) and an KSWNT of 15000 L/mol [50], SWNT fluorescence can be modeled for different protein concentrations. Modeling indicates that such a glucose sensing system is useful for detection of biologically relevant glucose concentrations (2-30 mM) and that the sensor response can be tuned based solely on protein concentration. Modeling indicates that practically useful levels of performance and sensor response can be obtained for reasonable protein concentrations in the range of tenths of mM.

Use of a Functionalized Polymer as a Sensing Polymer.

Tween 20™ (a polyoxyethylene sorbitan fatty acid ester, specifically olyoxyethylene sorbitan monolaurate ester) was functionalized with biotin (biotin-long chain-PEO-amine) employing 1,1 carbonyldiimidazole (CM) (51). The biotinylated Tween 20 (BioTween) was then immobilized on the surface of the nanotube using the dialysis procedure described above. The resulting nanotube solutions were free of visible aggregates and were stable stored at 4 C for >3 months.

Functionalization of Tween 20 for Biospecificity:

Tween 20 was reacted with CDI in DMSO (dried with molecular sieves) for 2 hr at 40° C. with mixing under a $N_2$ blanket. The product was precipitated using diethyl ether, and the collected material was redissolved and precipitated twice more to ensure removal of reaction byproducts. To add a biotin functional group to Tween, the CDI functionalized Tween was allowed to react with biotin-long chain-PEO-amine in standard Tris buffer (pH 7.4) for 24 hr at room temperature with mixing. Tween 20 and carbonyldiimidazole (CDI) were purchased from Sigma Aldrich (St. Louis, Mo.). Biotin-long chain-polyethylene oxide (PEO)-amine was purchased from Pierce.

Suspension of SWNT with Functionalized Tween.

Single walled carbon nanotubes were suspended in 2 wt % sodium cholate in nanopure $H_2O$ using a high intensity sonication method previously demonstrated to yield individually dispersed nanotubes. Functionalized Tween was added to the nanotube suspension in the ratio of 1:3. The resulting mixture was placed into a 10,000 molecular weight cutoff dialysis cassette and dialyzed against surfactant free buffer for 24 hrs, with the buffer being replaced at the 4 hr mark. The resulting solution shows no signs of aggregation and is stable for >1 month. The single walled carbon nanotubes used in this study were obtained from CNI, reactor run 107. To measure nanotube fluorescence, individually dispersed single walled carbon nanotubes were excited with a 785 nm photodiode laser (Invictus) and the resulting fluorescence emission was collected at 180° through a notch filter and shown onto a thereto-electrically cooled nIR CCD camera (Andor)

Changes in the SWNT photoluminescence during the removal of cholate by dialysis and the subsequent assembly of BioTween on the surface of the nanotube was monitored using a 785 nm photodiode laser. The fluorescence spectra obtained before and after a 20 hr dialysis against surfactant free buffer show that nanotube fluorescence decreases and emission from the (6,5) nanotube exhibits a shift to lower energy. Monitoring fluorescence decrease as a function of time shows a gradual decrease with time. However, closer inspection of the fluorescence data shows that both features do not decrease at the same rate. Emission from the (65) nanotube decreases at a faster rate than that of the (7,5) nanotube. This effect saturates at approximately 10 hrs.

As a control, Tween 20 functionalized with 1,1 carbonyl-diimidazole was allowed to react with water, creating an ionic Tween surfactant (HydroTween). This HydroTween was also assembled on the surface of the nanotube while monitoring SWNT optical properties. Assembly of the HydroTween on the surface of the nanotube shows similar behavior to that of the BioTween, with nanotube fluorescence decreasing during assembly and the surfactant showing similar selectivity between (6,5) and (7,5) nanotube species. However, in the case of assembly of HydroTween the selective decrease effect saturates after only 4 hrs. These results indicate that the biotin moiety does not act as a fluorescence quencher. However, it appears that biotin plays a role in the assembly process as evidenced by the differences in assembly time observed for complexes of BioTween and HydroTween. Attempts to suspend nanotubes with non-functionalized Tween 20 were unsuccessful, likely due to the non-ionic nature of the non-functionalized surfactant. It is believed that the end groups of Tween 20 are not sufficiently long to prevent SWNT-SWNT interactions from occurring. It was also found that highly functionalized samples of BioTween were also unsuccessfully for solubilization and suspension of SWNT. Tween 20 functionalized with CDI has three potential sites for further functionalization. Partial functionalization of Tween 20 with biotin leaves some remaining carboxylic acid groups. The presence of these carboxylic acid groups is believed to impart a partial negative charge to the surfactant causing charge-charge repulsion and sufficient hindrance to prevent nanotube tube aggregation.

Streptavidin Binding to the BioTween-SWNT Complex.

Total internal reflection (TIR) fluorescence microscopy, capable of single molecule fluorescence measurements, was employed to assess streptavidin binding to the BioTween-SWNT complex.

To first determine if the biotin in the BioTween/SWNT complex was still available for binding, a streptavidin coated surface was prepared by contacting biotinylated BSA immobilized non-specifically on a surface with streptavidin. The streptavidin coated surface was then washed with a dilute BioTween/SWNT solution. If the biotin in the complex remains capable of binding to streptavidin, nanotubes should remain immobilized on the surface. The treated surface potentially having immobilized BioTween/SWNT complexes was washed with quantum dots coated in streptavidin. Fluorescence microscope measurements show the presence of linear nanotube-like structures indicating that nanotubes are bound to the surface. A control surface treated with BioTween without nanotubes which was washed with quantum dots coated in streptavidin showed no fluorescing linear structures. These results indicate that the biotin in the BioTween/SWNT complex remains free to bind to biotin binding partners. (e.g., streptavidin and avidin).

Upon the addition of 2.02 microM streptavidin to the BioTween-SWNT complex, a significant decrease in fluorescence from the (6,5) nanotube was observed. This decrease occurred over 1-2 h, with an increase in the noise occurring after ~0.5 hr. Streptavidin is a tetramer with 4 biotin binding sites, the increase in the noise is believed to be due to nanotube aggregation induced by multiple binding events. The noise is decreased by shear mixing of the solution, consistent with disruption of aggregation. However, after a sufficient amount of time, the BioTween-SWNT streptavidin aggregates reform. If streptavidin binding sites are partially saturated with biotin prior to addition to BioTween-SWNT a fluorescence decrease is still observed. The results indicate that unblocked streptavidin can bind to more than one BioTween/SWNT complex.

The change in fluorescence of the BioTween/SWNT complex changes as a function of the amount of protein (streptavidin or avidin) added to a sensing composition containing the complex. Increasing protein concentration results in larger decreases in fluorescence. In contrast, addition of bovine serum albumin (BSA), a protein which is known to exhibit a high degree of non-specific binding to surfaces, to the BioTween/SWNT complex caused no fluorescent response. Thus, the observed changes in fluorescence are due to specific binding of the protein to the biotin moiety of the complex rather than to non-specific binding of protein to the nanotube.

REFERENCES

1. M. S. Dresselhaus, G. Dresselhaus, P. C. Eklund, *Science of fullerenes and carbon nanotubes* (Academic Press, San Diego, 1996).
2. R. Saito, G. Dresselhaus, M. S. Dresselhaus, *Physical Properties of Carbon Nanotubes* (Imperial College Press, London, 1998).
3. M. S. Gudiksen, L. J. Lauhon, J. Wang, D. C. Smith, C. M Lieber, *Nature* 415, 617-620 (Feb. 7, 2002).
4. T. Durkop, S. A. Getty, E. Colas, M. S. Fuhrer, *Nano Letters* 4, 35-39 (2004).
5. R. J. Chen at al., *Proceedings of the National Academy of Sciences of the United States of America* 100, 4984-4989 (Apr. 29, 2003).
6. J. Li et al., *Nano Letters* 3, 929-933 (July, 2003).
7. L. J. McCartney, J. C. Pickup, O. J. Rolinski, D. J. S. Birch, *Analytical Biochemistry* 292, 216-221 (May 15, 2001).
8. L. L. E. Salins, R. A. Ware, C. M. Ensor, S. Daunert, *Analytical Biochemistry* 294, 19-26 (Jul. 1, 2001).
9. A. Heller, *Annual Review of Biomedical Engineering* 1, 153-175 (1999).
10. M, J. O'Connell at al., *Science* 297, 593-596 (Jul. 26, 2002).
11. S. M. Bachilo at al., *Science* 298, 2361-2366 (Dec. 20, 2002).
12, S. Wray, M. Cope, D. Delpy, J. Wyatt, E. Reynolds, *Biochimica at Biophsica Acta* 933, 184-192 (1988).
13. M. S. Strano et al. *Journal of Nanoscience and Nanotechnology* 3, 81-86 (February-April, 2003).
14. M. Zheng et al., *Science* 302, 1545-1548 (Nov. 28, 2003).
15. M. Zheng et al., *Nature Materials* 2, 338-342 (2003).
16. M. S. Strano et al., *Science* 301, 1519-1522 (Sep. 12, 2003).
17. M. S. Strano et al., *Journal of Physical Chemistry B* 107, 6979-6985 (Jul. 24, 2003).
18. L. Xia, R. L. McCreery, *Journal of the Electrochemical Society* 146, 3696-3701 (October, 1999).
19. X. M. Dou, Y. Ozaki, *Applied Spectroscopy* 52, 815-819 (June 1998).
20. V. Saxena, M. Sadoqi, J. Shao, *J. of Pharm. Sci.* 92, 2090-2097 (2003).
21. Hartschuh, A. et at Simultaneous fluorescence and Raman scattering from single carbon nanotubes. *Science* 301, 1354-1356 (2003).
22. Moore, V. C. et al. Individually suspended single-walled carbon nanotubes in various surfactants. *Nano Letters* 3, 1379-1382 (2003).
23. Bahr, J. L. and Tour, J. M. Covalent chemistry of single-walled carbon nanotubes. *J. Mat. Chem.* 12, 1952-1958 (2002).
24. Bahr, J. L. et al. Functionalization of Carbon Nanotubes by Electrochemical Reduction of Aryl Diazonium Salts: Bucky Paper Electrode. *J. Am. Chem. Soc.* 123, 6536-6542 (2001).
25 Reich, S. et al., Tight-binding description of graphene. *Physical Review B,* 2002. 66(3); p. 035412.
26 Saito, R., G. Dresselhaus, and M. S. Dresselhaus, *Trigonal warping effect of carbon nanotubes. Physical Review B,* 2000. 61(4): p. 2981-2990.
27 Bronikowski, M. J. et al., *Gas-phase method for large-scale production of single-walled carbon nanotubes. Abstracts of Papers of the American Chemical Society,* 2000. 219: p. 421-PHYS
28 Bronikowski, M. J., et al., *Gas-phase production of carbon single-walled nanotubes from carbon monoxide via the HiPco process: a parametric study.* J. Vac. Sci. Tech. A, 2001. 19(4): p. 1800-1804.
29 M. S. Dresselhaus, a Dresselhaus, P. Avouris, Eds. Carbon Nanotubes: Synthesis, Structure, Properties, and Applications, vol. 80 (Springer Berlin, 2001)
30 S. M. Bachilo, L. Balzano, J. E. Herrera, F. Pompeo, D. E. Resasco and R. B. Weisman, "Narrow (n,m)-Distribution of Single-Walled Carbon Nanotubes Grown using a Solid Supported Catalyst"*J. Am. Chem. Soc.* 125 (2003) 11186-11187.
31 Klueh, U.; Dorsky, D. L; Kreutzer, D. L. Enhancement of implantable glucosesensor function in vivo using gene transfer-induced neovascularization. *Biomaterials* 2005, 26, 1155-1163.
32 Vales, T. L; Klueh, U.; Kreutzer, D.; Moussy, F. Ex ova chick chorioaliantoic membrane as a novel in vivo model for testing biosensors. *Journal of Biomedical Materials Research Part A* 2003, 67A, 215-223.
33 Rebrin, K; Fischer, U.; Vondorsche, H. H.; Vonwoetke, T.; Abel, P. et al. Subcutaneous Glucose Monitoring by Means of Electrochemical Sensors—Fiction or Reality. *Journal of Biomedical Engineering* 1992, 14, 33-40.
34 Abel, P. U.; von Woedtke, T. Biosensors for in vivo glucose measurement: can we cross the experimental stage. *Biosensors & Bioelectronics* 2002, 17, 1059-1070.
35 Gerritsen, M.; Paquay, Y. G. C. J.; Jansen, J. A. Evaluation of the tissue reaction to a percutaneous access 35 device using titanium fibre mesh anchorage in goats, *Journal of Materials Science-Materials in Medicine* 1998, 9, 523-528.
36 Galeska, I.; Hickey, T.; Moussy, F.; Kreutzer, D.; Papadimitrakopoulos, F. Characterization and biocompatibility studies of novel humic acids based films as membrane material for an implantable glucose sensor. *Biomacromolecules* 2001, 2, 1249-1255.
37 Clark, H.; Barbari, T. A.; Stump, K.; Rao, G. Histologic evaluation of the inflammatory response around implanted hollow fiber membranes. *Journal of Biomedical Materials Research* 2000, 52, 183-192.
38 Ward, W. K.; Quinn, M. J.; Wood, M. D.; Tiekotter, K. L.; Pidikiti, S. et al. Vascularizing the tissue surrounding a model biosensor: how localized is the effect of a subcutaneous infusion of vascular endothelial growth factor (VEGF)? *Biosensors & Bioelectronics* 2003, 19, 155-163.
39 Klueh, U.; Dorsky, D. I.; Kreutzer, D. L. Use of vascular endothelial cell growth factor gene transfer to enhance implantable sensor function in vivo. *Journal of Biomedical Materials Research Part A* 2003, 67A, 1072-1086.
40 Levy, A. P.; Levy, N. S.; Loscaizo, J.; Calderone, A. Takahashi, N. et al. Regulation of Vascular Endothelial Growth-Factor in Cardiac Myocytes. *Circulation Research* 1995, 76, 758-766,
41 McColm, J.; Cunningham, S. The development of a computer controlled system to simulate in rats, the rapid, frequent changes in oxygen experienced by preterm infants developing retinopathy of prematurity. *Journal of Medical Engineering & Technology* 2000, 24, 45-52.
42 Pisano, C.; Aulicino, C.; Vesci, L.; Casu, B.; Naggi, A. et al. Undersulfated, low molecular-weight glycol-split heparin as an antiangiogenic VEGF antagonist. *Glycobiology* 2005, 15, 1c-6c.
43 Rusnati, M.; Urbinati, C.; Caputo, A.; Possati, L.; Lortat-Jacob, H. et al. Pentosan polysulfate as an inhibitor of extracellular HIV-1 Tat. *Journal of Biological Chemistry* 2001, 276, 22420-22425.
44 Uhlmann, S.; Friedrichs, U.; Eichler, W.; Hoffmann, S.; Wiedemann, P. Direct measurement of VEGF-induced nitric oxide production by choroidal endothelial cells. *Microvascular Research* 2001, 62, 179-189.
45 Cherukuri, P.; Bachilo, S. M.; Litovsky, S. H.; Weisman, R. B. Near-infrared fluorescence microscopy of single-walled carbon nanotubes in phagocyte cells. *Journal of the American Chemical Society* 2004, 126, 15638-15639.
46 Norton, L. W.; Tegnell, E.; Toporek, S. S.; Reichert, W. M. In vitro characterization of vascular endothelial growth factor and dexamethasone releasing hydrogels for implantable probe coatings. *Biomaterials* 2005, 26, 3285-3297.
47 Anseth, K. S.; Metters, A. T.; Bryant, S. J.; Martens, P. J.; Elisseeff, J. H. et al. In situ forming degradable networks and their application in tissue engineering and drug delivery. *Journal of Controlled Release* 2002, 78, 199-209.
48. Elisseeff, J.; McIntosh, W.; Fu, K.; Blunk, T.; Langer, R. Controlled-release of IGF-I and TGF-beta 1 in a photopolymerizing hydrogel for cartilage tissue engineering. *Journal of Orthopaedic Research* 2001, 19, 1098-1104.
50 Cascone, M. G.; Laus, M.; Ricci, D.; Delguerra, R. S. Evaluation of Poly(VinylAlcohol) Hydrogels as a Component of Hybrid Artificial Tissues. *Journal of Materials Science-Materials in Medicine* 1995, 6, 71-75.
51 Schultz, J. S.; Mansouri, S.; Goldstein, I. J. Affinity Sensor—a New Technique for Developing implantable Sensors for Glucose and Other Metabolites. *Diabetes Care* 1982, 5, 245-253.
52 Chen, R. J.; Bangsaruntip, S.; Drouvalakis, K. A.; Kam, N. W. S.; Shim, M.; Li, V. M.; Kim, W.; Utz, P. J.; Dai, H. J. Noncovalent functionalization of carbon nanotubes for highly specific electronic biosensors. *Proceedings of the National Academy of Sciences of the United States of America* 2003, 100, 4984-4989.
53 Chen, J., et al., Solution properties of single-walled carbon nanotubes. Science, 1998. 282(5386): p. 95-98.
54 Nakashima, N., Y. Tomonari, and H. Murakami, *Water-soluble single-walled carbon nanotubes via noncovalent sidewall-functionalization with a pyrene-carrying ammonium ion*. Chemistry Letters, 2002(6): p. 638-639.
55 Huang, W. J., et al., *Sonication-assisted functionalization and solubilization of carbon nanotubes*. Nano Letters, 2002. 2(3): p. 231-234.
56 Chen, J., at al., *Dissolution of full-length single-walled carbon nanotubes*. Journal of Physical Chemistry B, 2001. 105(13): p. 2525-2528.
57 Bronikowski, M. J., et al., *Gas-phase method for large-scale production of single-walled carbon nanotubes*. Abstracts of Papers of the American Chemical Society, 2000. 219: p. 421-PHYS.

What is claimed is:

1. An analyte sensing composition for detecting an analyte, or determining the concentration of the analyte, which comprises a sensing complex of a sensing protein with a semi-conducting, single-walled nanotube consisting of carbon, wherein the carbon nanotube of the sensing complex is emissive, having an optical property of photoinduced band gap fluorescence in the near-infrared, the sensing protein selectively binds to or selectively reacts with the analyte, and the photo-induced band gap fluorescence of the carbon nanotube of the sensing complex is responsive to the selective binding of the sensing protein to the analyte or the selective reaction of the sensing protein with the analyte, the selective binding of the sensing protein with the analyte providing an altered emissive effect, wherein the sensing protein is an enzyme which catalyzes oxidation or reduction of the analyte and wherein the sensing composition further comprises one or more redox mediators which function for electron transfer from the analyte or the oxidation or reduction product thereof to the complexed carbon nanotube.

2. The analyte sensing composition of claim 1, wherein the sensing protein is covalently bonded to the analyte.

3. The analyte sensing composition of claim 1, wherein the sensing protein comprises one or more epitopes which bind to an antibody or antibody fragment.

4. The analyte sensing composition of claim 1, wherein the enzyme selected from the group consisting of a glucose oxidase a glucose dehydrogenase, a galactose oxidase, a glutamate oxidase, an L-amino acid oxidase, a D-amino acid oxidase, a cholesterol oxidase, a cholesterol esterase, a choline oxidase, a lipoxigenase, a lipoprotein lipase, a glycerol kinase, a glycerol-3-phosphate oxidase, a lactate oxidase, a lactate dehydrogenase, a pyruvate oxidase, an alcohol oxidase, a bilirubin oxidase, a sarcosine oxidase, a uricase, and an xanthine oxidase.

5. The analyte sensing composition of claim 1, wherein the analyte sensing composition is dispersed in a liquid phase.

6. The analyte sensing composition of claim 5, wherein the analyte sensing composition is dispersed in an aqueous medium.

7. The analyte sensing composition of claim 1, wherein the analyte sensing composition is dispersed in a solid or semi-solid matrix wherein the matrix is selectively permeable to the analyte, but not permeable to the sensing complex.

8. The analyte sensing composition of claim 1, wherein the nanotube of the sensing complex has a 1-D electronic structure and an optical property of photoinduced band gap fluorescence in the near-infrared and the photo-induced band gap fluorescence of the carbon nanotube of the sensing complex is responsive to the selective reaction of the sensing protein with the analyte while maintaining the 1-D electronic structure of the carbon nanotube.

9. A sensing element for detecting an analyte, wherein the sensing element comprises: (a) the analyte sensing composition of claim 1, and (b) a selectively porous container for receiving, and retaining the analyte sensing composition, wherein the container is sufficiently porous to allow the analyte to enter the container without allowing the sensing complex of the sensing polymer protein with the semi-conducting, single-walled carbon nanotube of the analyte sensing composition to exit the container.

10. A sensing system for detecting one or more analytes, wherein the sensing system comprises: (a) one or more sensing elements of claim 9; (b) a source of electromagnetic radiation for exciting the photo-induced band gap fluorescence in the near-infrared of the carbon nanotube of the sensing complex; and (c) a detector for detecting the photo-induced band gap fluorescence of the carbon nanotube of the sensing complex.

11. The sensing system of claim 10, wherein the one or more sensing elements are capable of being implanted within a mammal.

12. A sensing element for detecting an analyte, wherein the sensing element comprises: (a) the analyte sensing composition of claim 1, and (b) a selectively porous container for receiving and retaining the analyte sensing composition, wherein the container is sufficiently porous to allow the analyte to enter the container without allowing the sensing complex of the sensing protein with the semi-conducting, single-walled carbon nanotube of the analyte sensing composition to exit the container.

13. A sensing element for detecting a monosaccharide, wherein the sensing comprises: (a) the analyte sensing composition of claim 1; and (b) a selectively porous container for receiving and retaining the analyte sensing composition, wherein the container is sufficiently porous to allow the monosaccharide to enter the container without allowing the sensing complex of the protein with the semi-conducting, single-walled carbon nanotube of the analyte sensing composition to exit the container.

14. A sensing system for detecting one or more analytes, wherein the sensing system comprises: (a) one Or more sensing elements for detecting an analyte of claim 12; (b) a source of electromagnetic radiation for exciting the photo-induced band gap fluorescence in the near-infrared of the carbon nanotube of the sensing complex; and (c) a detector for detecting the photo-induced band gap fluorescence in the near-infrared of the carbon nanotube of the sensing complex.

15. The sensing system of claim 14, wherein the analyte is glucose.

16. The sensing system for detecting one or more monosaccharides, wherein the sensing system comprises: (a) one or more sensing elements for detecting a monosaccharide of claim 12; (b) a source of electromagnetic radiation for exciting the photo-induced band gap fluorescence in the near infrared of the carbon nanotube of the sensing complex; and (c) a detector for detecting the photo-induced band gap fluorescence in the near-infrared of the carbon nanotube of the sensing complex.

17. The sensing system of claim 16 wherein the analyte is glucose.

18. An analyte sensing composition for detecting an analyte, or determining the concentration of the analyte, which comprises a sensing complex which consists essentially of a sensing protein and a semi-conducting, single-walled nanotube consisting of carbon, wherein the carbon nanotube of the sensing complex is emissive, having an optical property of photo-induced band gap fluorescence in the near-infrared, the sensing protein selectively binds to or selectively reacts with the analyte, and the photo-induced band gap fluorescence of the carbon nanotube of the sensing complex is responsive to the selective binding of the sensing protein to the analyte or the selective reaction of the sensing protein with the analyte, the selective binding of the sensing protein with the analyte providing an altered emissive effect wherein the sensing protein is an enzyme which catalyzes oxidation or reduction of the analyte and wherein the sensing composition further comprises one or more redox mediators which function for electron transfer from the analyte or the oxidation or reduction product thereof to the complexed carbon nanotube.

19. The sensing system of claim 10, wherein at least one of the one or more sensing elements is capable of being implanted within a mammal.

20. The sensing system of claim 19, wherein the mammal is a human.

21. The sensing system of claim 14, wherein at least one of the one or more sensing elements is capable of being implanted within a mammal.

22. The sensing system of claim 21, wherein the mammal is a human.

* * * * *